US008685375B2

(12) United States Patent
Arditty et al.

(10) Patent No.: US 8,685,375 B2
(45) Date of Patent: Apr. 1, 2014

(54) SOLID COSMETIC COMPOSITION FOR APPLICATION TO KERATIN FIBRES

(75) Inventors: Stephane Arditty, Ballainvilliers (FR);
Florence Lahousse, Thiais (FR);
Nathalie Jager Lezer, Verrieres-le-Buisson (FR)

(73) Assignee: L'Oreal, Paris (FR)

( * ) Notice: Subject to any disclaimer, the term of this patent is extended or adjusted under 35 U.S.C. 154(b) by 774 days.

(21) Appl. No.: 12/617,520

(22) Filed: Nov. 12, 2009

(65) Prior Publication Data

US 2010/0242984 A1    Sep. 30, 2010

Related U.S. Application Data

(60) Provisional application No. 61/121,291, filed on Dec. 10, 2008.

(30) Foreign Application Priority Data

Nov. 24, 2008    (FR) ..................... 08 57976

(51) Int. Cl.
*A61Q 5/00*    (2006.01)

(52) U.S. Cl.
USPC ..... 424/70.1; 424/70.6; 424/70.7; 424/70.22; 424/70.23; 424/70.24; 424/70.31; 424/401; 514/787

(58) Field of Classification Search
USPC ................ 424/70.1, 70.6, 70.7, 70.22, 70.23, 424/70.24, 70.31, 401; 514/787
See application file for complete search history.

(56) References Cited

U.S. PATENT DOCUMENTS

| | | | |
|---|---|---|---|
| 2,007,245 A | | 7/1935 | Gimonet |
| 2,263,632 A * | | 11/1941 | Kendall ............ 401/82 |
| 2,925,819 A * | | 2/1960 | Altman ............ 401/19 |
| 3,937,811 A | | 2/1976 | Papantoniou et al. |
| 5,085,856 A * | | 2/1992 | Dunphy et al. ........ 424/64 |
| 5,162,410 A | | 11/1992 | Sweet |
| 5,389,363 A | | 2/1995 | Snyder et al. |
| 5,616,746 A * | | 4/1997 | Mahieu et al. ......... 554/66 |
| 5,763,497 A * | | 6/1998 | Ikeda et al. .......... 424/401 |
| 5,874,069 A | | 2/1999 | Mendolia et al. |
| 5,919,441 A | | 7/1999 | Mendolia et al. |
| 5,981,680 A | | 11/1999 | Petroff et al. |
| 6,051,216 A | | 4/2000 | Barr et al. |
| 6,325,995 B1 * | | 12/2001 | El-Nokaly et al. ........ 424/64 |
| 6,491,927 B1 | | 12/2002 | Arnaud et al. |
| 2002/0182157 A1 * | | 12/2002 | Grayson ............. 424/64 |
| 2005/0249687 A1 | | 11/2005 | Farer et al. |
| 2008/0095566 A1 | | 4/2008 | Thiebaut et al. |
| 2010/0215605 A1 * | | 8/2010 | Arditty et al. ........ 424/70.11 |

FOREIGN PATENT DOCUMENTS

| | | |
|---|---|---|
| DE | 198 26 118 A1 | 12/1999 |
| DE | 102 33 288 A1 | 2/2004 |
| EP | 0 662 312 A1 | 7/1995 |
| EP | 0 955 039 A1 | 11/1999 |
| EP | 1 068 854 A1 | 1/2001 |
| EP | 1 086 945 A1 | 3/2001 |
| EP | 1 396 259 A2 | 3/2004 |
| EP | 1 410 787 A1 | 4/2004 |
| EP | 1 411 069 A2 | 4/2004 |
| EP | 1 473 017 A1 | 11/2004 |
| EP | 1 745 771 A1 | 1/2007 |
| EP | 1 894 602 A1 | 3/2008 |
| EP | 1 913 835 A1 | 4/2008 |
| FR | 2 232 303 A1 | 1/1975 |
| FR | 2 792 190 A1 | 10/2000 |
| FR | 2 833 163 A1 | 6/2003 |
| WO | WO 93/23008 A1 | 11/1993 |
| WO | WO 02/39961 A1 | 5/2002 |
| WO | WO 02/47031 A2 | 6/2002 |
| WO | WO 2004/028488 A2 | 4/2004 |
| WO | WO 2004/055081 A2 | 7/2004 |
| WO | WO 2004/073626 A2 | 9/2004 |
| WO | WO 2006/057439 | 6/2006 |
| WO | WO 2008/046763 A1 | 4/2008 |

OTHER PUBLICATIONS

Griffen, "Calculation of HLB Values of Non-ionic Surfactants," *Journal of the Society of Cosmetics Chemists*, 1954, vol. 5, pp. 249-256.
"Surfactants and Detersive Systems," *Encyclopedia of Chemical Technology*, Kirk-Othmer, 1979, vol. 22, 3$^{rd}$ Edition, pp. 332-432.
Prince, "Microemulsions Theory and Practice," 1977, pp. 21-32.
"Specialist Surfactants," Edited by ROBB, Chapter 8 by TERECH, 1997, pp. 208-263.
French Search Report issued in French Patent Application No. 0857976 on Jul. 16, 2009 (w/ English-language translation).

* cited by examiner

*Primary Examiner* — Ali Soroush
(74) *Attorney, Agent, or Firm* — Oliff PLC

(57) ABSTRACT

The present invention relates to a cosmetic composition for caring for and/or making up keratin fibers, in stick form, which can be applied dry, (i), in the form of an emulsion comprising a fatty phase dispersed in an aqueous phase, the said fatty phase comprising carnauba wax and/or synthetic beeswax, in a content of at least 2% by weight relative to the total weight of the said composition, and (ii) having a shear hardness of between 375 g/m and 5000 g/m, the said shear hardness being measured at 20° C. on a cylindrical stick using a rigid tungsten wire 250 μm in diameter, by advancing the wire relative to the stick at a rate of 100 mm/minute. The invention also relates to the process for coating keratin fibers comprising at least one step of applying a composition in accordance with the invention.

15 Claims, 3 Drawing Sheets

SOLID COSMETIC COMPOSITION FOR APPLICATION TO KERATIN FIBRES

Figure 1:
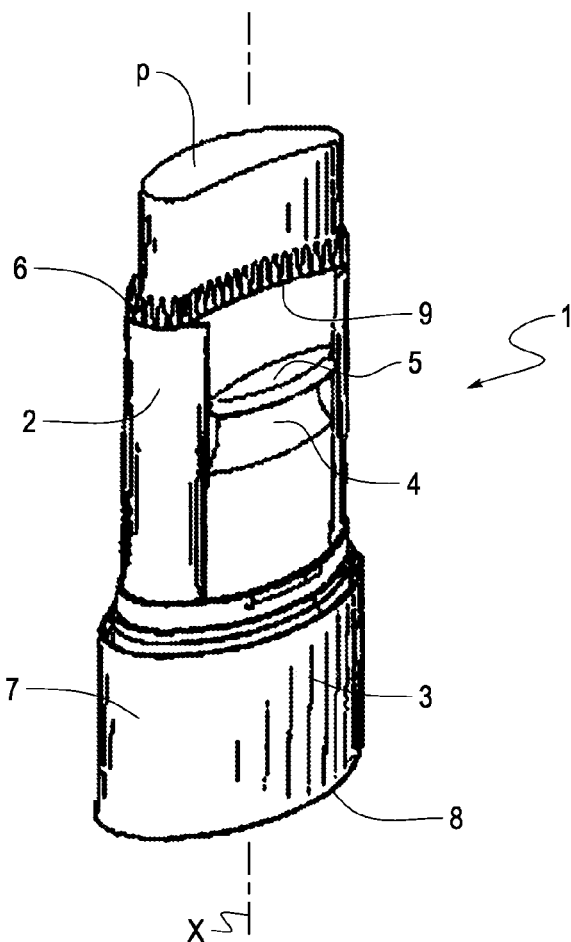

The present invention relates to a care and/or make up cosmetic composition in stick form, for caring for and/or making up keratin fibres and especially the eyelashes.

The term "keratin fibres" means the eyelashes, the eyebrows, bodily hair or head hair.

More particularly, the invention relates to a mascara.

The term "mascara" means a composition intended to be applied to keratin fibres, especially to the eyelashes: it may be an eyelash makeup composition, an eyelash makeup base (also known as a base coat), a composition to be applied onto a mascara (also known as a top coat), or a cosmetic eyelash treatment composition. The mascara is more particularly intended for human eyelashes, but also false eyelashes.

In general, two types of mascara are distinguished according to their formulation: (i) washable mascaras that can be cleansed with water or soapy water and that are generally in the form of a wax-in-water emulsion, such as creams or gels, and (ii) waterproof mascaras, which require the use of an oily formulation in order to be removed and which are generally formulated in the form of a dispersion of wax in organic solvents.

The present invention relates to the particular type of mascaras known as washable mascaras.

The most conventional mascaras usually have a pasty texture and are conditioned in a container comprising a reservoir equipped with a drainer and an applicator, especially in the form of a brush or a comb, and which are applied by taking up product in the reservoir using the applicator, passing the applicator through the drainer in order to remove the excess product, and then placing the applicator impregnated with mascara in contact with the eyelashes.

Mascaras in solid form, also known as "cake mascaras", which are compositions comprising a high proportion of waxes, pigments and surfactants, and which can be eroded with water, i.e. they require, prior to being applied to the eyelashes, contact with an aqueous phase so as to partially dissolve the mascara cake, are also known, for example from documents U.S. Pat. No. 2,007,245 and FR 2 833 163. In particular, the application takes place via a brush impregnated with water, which is placed in contact with the mascara, and the mixture taken up is then applied to the eyelashes with the brush so as to deposit the material onto the eyelashes.

Document WO 2006/057 439 also describes mascara compositions that are solid at room temperature, which are softened using a device that increases the temperature so as to be able to be applied to the eyelashes. Once the softened mascara composition has been applied to the eyelashes, it is quickly cooled and thus solidifies, allowing the formation of a firm film covering the eyelashes. This composition is in the form of an oily mixture in which a hydrophobic solid compound forms the fatty phase.

However, the use of these compositions may prove to be long and laborious, requiring great dexterity by the user. In other words, several manipulations precede the application per se to the eyelashes. Furthermore, such "cake mascaras" or solid mascaras may require special implementation devices comprising several components that might be expensive.

Another formulation route for a composition for coating keratin fibres, especially the eyelashes, consists of a stick that in particular enables a practical application of the coating composition to the eyelashes, by direct transfer of the said composition to the eyelashes via simple dry application, without the intermediacy of a brush impregnated with water or of any heating device.

Sticks have already been developed in cosmetics, especially for the purposes of making up and/or caring for keratin materials, certain references for which are cited hereinbelow. Among these sticks, intended for making up and/or caring for keratin materials, some are in the form of a solid water-in-oil emulsion comprising an aqueous phase emulsified with a surfactant in a fatty phase, the said fatty phase comprising an oil, a wax and a block copolymer. Document EP 1 473 017 describes such a type of solid inverse emulsion. However, these sticks typically have a texturometry hardness markedly greater than 5000 g/m, which is too hard to be compatible with an application more specific to keratin fibres. In other words, such sticks of the prior art are unsuitable for the application intended in the present patent application.

The development of compositions in stick form that can be applied dry for making up and/or caring for keratin fibres thus presents a certain number of difficulties. These difficulties lie especially in obtaining a stick of controlled hardness conditioning the amount of material deposited on the keratin fibres, especially on the eyelashes, the quality of the deposit, and also the speed and ease of applying the makeup for the user.

Document EP 1 745 771 relating to a process for coating keratin fibres describes compositions in stick form that can be applied dry and that have a hardness ranging from 500 to 18 200 Pa, and expressed according to the protocol described below ranging from 320 g/m to 11 657 g/m. However, the compositions illustrated in that document not only target anhydrous compositions of waterproof type, but also target compositions whose hardnesses do not allow the production of a stick suitable for an application of mascara type that satisfies the controlled hardness requirements recalled hereinabove.

Specifically, a stick that is too hard or too soft will not be able to produce a quality deposit on the eyelashes, especially a sufficient and uniform deposit that satisfactorily coats the eyelashes, and will be detrimental to the practical and rapid aspect of the application. It should be noted that a stick that is too hard will not enable sufficient deposition of product onto the eyelashes, whereas a stick that is too soft will run the risk of producing a non-uniform deposit, or even a deposit in the form of unattractive lumps on the eyelashes. Furthermore, a product paste that is too soft will hamper the production of a stick with a sufficient impact strength and pressure resistance, especially at the time of its application.

There is thus still a need for a stick that is sufficiently solid and rigid to ensure its resistance at the time of its application, but also sufficiently soft and erodible when dry so as to enable suitable coating of the eyelashes comparable to that obtained with the most conventional mascaras currently on the market.

The inventors have now discovered, surprisingly, that it is possible to obtain a composition that satisfies these requirements by producing a composition that is in the form of a dispersion of a fatty phase in an aqueous phase, characterized by its hardness and by the presence of carnauba wax and/or synthetic beeswax in a particular content. The inventors have thus discovered a composition of "washable" type with a shear hardness that is compatible with the formation on the eyelashes of a quality deposit of satisfactory thickness, which appropriately coats the eyelashes.

According to a first aspect, the present invention is directed towards a cosmetic composition in stick form, which can be applied dry, for caring for and/or making up keratin fibres, (i) which is in the form of an emulsion comprising a fatty phase dispersed in an aqueous phase, the said fatty phase comprising carnauba wax and/or synthetic beeswax, in a content of at least 2% by weight, preferably at least 3% by weight, advantageously at least 4% by weight, or even from 5% to 30% by weight, relative to the total weight of the said composition, and (ii) which has a shear hardness of between 375 g/m and 5000 g/m, the said shear hardness being measured at 20° C. on a cylindrical stick, using a rigid tungsten wire 250 µm in diameter, by advancing the wire relative to the stick at a rate of 100 mm/minute.

The presence of a minimum content of specific waxes such as carnauba wax and/or synthetic beeswax in the composition according to the invention appears to allow better structuring of its aqueous phase, thus making it possible to use a dry extract in smaller amount in the said composition of wax-in-water type, contrary to the use of other waxes that require the presence of a solids content of greater than 45% by weight relative to the total weight of the composition, which is detrimental to the quality of the deposit on the eyelashes.

According to one particular embodiment, the composition according to the invention has a solids content of less than or equal to 45% by weight, in particular less than 45% by weight, especially greater than or equal to 25% by weight, in particular greater than or equal to 30% by weight and even more particularly greater than or equal to 35% by weight relative to the total weight of the said composition.

Such a composition is, moreover, advantageously able to be obtained, or even is obtained, via a process comprising at least one step that involves a removal of heat, allowing a lowering of the temperature of the composition to less than 4° C., or even less than 1° C., in less than 30 minutes.

According to another aspect, the invention is directed towards a cosmetic composition in stick form, which can be applied dry, for caring for and/or making up keratin fibres:

(i) which is in the form of an emulsion comprising a fatty phase dispersed in an aqueous phase, the said fatty phase comprising carnauba wax and/or synthetic beeswax, in a content of at least 2% by weight, preferably at least 3% by weight, advantageously at least 4% by weight, or even from 5% to 30% by weight, relative to the total weight of the said composition, (ii) which has a shear hardness of between 375 g/m and 5000 g/m, the said shear hardness being measured at 20° C. on a cylindrical stick, using a rigid tungsten wire 250 µm in diameter, by advancing the wire relative to the stick at a rate of 100 mm/minute, and (iii) which is obtained via a process comprising at least one step that involves a removal of heat, allowing a lowering of the temperature of the composition to less than 4° C., or even less than 1° C., in less than 30 minutes.

According to yet another aspect, the invention is directed towards a process for coating keratin fibres, comprising at least the steps consisting in:
placing the said keratin fibres in contact with at least part of the surface of a stick comprising a cosmetic composition according to the invention; and then
effecting a relative movement between the surface of the said stick and the said keratin fibres, so as to bring about erosion of the said stick and the formation of a deposit of at least one coat of the said cosmetic composition on the said keratin fibres.

According to yet another aspect, the invention is directed towards a device for conditioning and applying a cosmetic composition for caring for and/or making up keratin fibres, comprising at least:
a) one stick comprising a cosmetic composition according to the invention;
b) one support for the said stick; and
c) optionally at least one application element, the said application element also possibly being equipped with members for separating and/or combing the said keratin fibres.

According to yet another aspect, the invention is directed towards a stick, which can be applied dry, for making up and/or caring for keratin materials, which may be obtained, or even is obtained, via the process comprising at least one of the following steps consisting successively in:
heating a fatty phase and an aqueous phase, the said fatty phase comprising carnauba wax and/or synthetic beeswax, in a content of at least 2% by weight relative to the total weight of the said composition, to a temperature of between 80° C. and 100° C. and more particularly between 85° C. and 100° C., for example to a temperature of 95° C.,
emulsifying the said phases especially using a stirrer so as to obtain a composition of emulsion type with an aqueous continuous phase,
hot-casting the said composition in a conditioning device, and then
cooling the said composition to temperature of between −30° C. and 10° C., for example less than −28° C., until the composition is in the form of a stick, especially for a time of between 15 and 60 minutes, for example 45 minutes.

According to this aspect, the stick advantageously has a shear hardness of between 375 g/m and 5000 g/m, the said shear hardness being measured at 20° C. on a stick using a rigid tungsten wire 250 µm in diameter, by advancing the wire relative to the stick at a rate of 100 mm/minute.

According to a final aspect, the invention relates to a stick, which can be applied dry, for making up and/or caring for keratin fibres,
(i) which is in the form of an emulsion comprising a fatty phase dispersed in an aqueous phase, the said fatty phase comprising carnauba wax and/or synthetic beeswax, in a content of at least 2% by weight, preferably of at least 3% by weight, advantageously at least 4% by weight, for even from 5% to 30% by weight, relative to the total weight of the said composition,
(ii) which has a shear hardness of between 375 g/m and 5000 g/m, the said shear hardness being measured at 20° C. on a stick using a rigid tungsten wire 250 µm in diameter, by advancing the wire relative to the stick at a rate of 100 mm/minute,
(iii) the said stick being obtained via a process comprising at least the following steps consisting successively in:
heating the said emulsion to a temperature of between 80° C. and 100° C. and more particularly between 85° C. and 100° C., for example to a temperature of 95° C.,
emulsifying the said phases especially using a stirrer so as to obtain a composition of emulsion type with an aqueous continuous phase,
hot-casting the said composition in a conditioning device, and then
removing heat, to allow a lowering of the stick temperature to less than 4° C., or even less than 1° C., in less than 30 minutes.

DEFINITIONS ACCORDING TO THE INVENTION

The term "stick" denotes a wand, of predetermined form, which, in the absence of a stress, at room temperature and atmospheric pressure, conserves its predetermined form. Thus conditioned in the form of a stick, the composition is said to be self-supporting, preferably for at least 60 seconds. The cross section of the stick may be of any shape, for example that appearing in the attached FIG. 1. The cross section may especially be "bean"-shaped, i.e. comprising a concave portion and a convex portion towards the interior, the said concave and convex portions extending along one side of larger dimension of a transverse section. The cross section may also be polygonal, especially square, rectangular, oval or elliptical.

The term "can be applied dry" means that the composition is capable of forming a deposit, which is preferably adherent and coating, on keratin fibres without needing to be placed in contact beforehand with an aqueous phase. The present characteristic "can be applied dry" clearly distinguishes the composition according to the present invention from cake mascaras that are erodible with water and that must be partially dissolved beforehand in order to be applied to the fibres and form an adherent and coating deposit.

The term "cylinder" means any solid comprising at least two opposite faces or bases, which are optionally flat, and where appropriate parallel, connected together via a set of mutually parallel generatrices. The term "cylinder" thus comprises not only solids having at least one base whose contour is closed by a curved guideline, but also solids of prism type having at least one base whose contour is closed by a guideline of edge type.

For the purposes of the present invention, the "solids content" denotes the content of non-volatile material.

The solids content (abbreviated as SC) of a composition according to the invention is measured using a commercial "Halogen Moisture Analyzer HR83" halogen desiccator from Mettler Toledo. The measurement is performed on the basis of the weight loss of a sample dried by halogen heating and thus represents the percentage of residual material once the water and the volatile materials have been evaporated off.

This technique is fully described in the machine documentation provided by Mettler Toledo.

The measuring protocol is as follows:

About 2 g of the composition, hereinbelow the sample, are spread out on a metal crucible, which is placed in the halogen desiccator mentioned above. The sample is then subjected to a temperature of 120° C. for one hour. The Wet Mass of the sample, corresponding to its initial mass, and the Dry Mass of the sample, corresponding to its mass after halogen drying, are measured using a precision balance.

The experimental error associated with the measurement is of the order of ±2%. The solids content is calculated in the following manner:

Solids Content(expressed as weight %)=100×(Dry Mass/Wet Mass)

The term "polymer" means compounds comprising at least two, preferably at least three and more especially at least ten repeating units.

FIG. 1 shows a perspective view in profile of a preferential embodiment of a device 1 according to the invention, the push-button being in the median position. The preferred conditioning device represented in FIG. 1 is shown merely as a guide and is not in any way a limitation of the invention.

Figure 2:
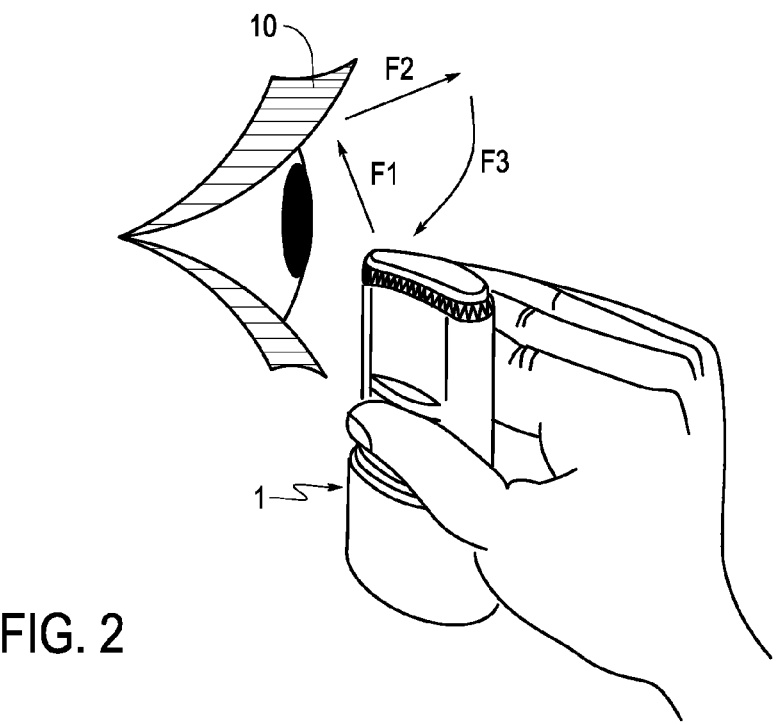

FIG. 2 constitutes a view during the use of a device 1 according to the invention.

The invention will now be described in greater detail.

Hardness

A cosmetic composition in stick form, which can be applied dry, for caring for and/or making up keratin fibres according to the invention has a shear hardness of between 375 g/m and 5000 g/m measured according to the method defined below.

With such a hardness, the composition is "soft" enough to allow direct and easy application to the eyelashes, especially deposition of material by simple placing in contact with the eyelashes, without exerting undue pressure on the eyelash fringe.

To determine the "shear hardness" of a stick in accordance with the invention, the "cheese wire" method may be used, which consists in transversely cutting a cylindrical stick, for example 8 mm in diameter, using a rigid tungsten wire 250 μm in diameter, by advancing the wire relative to the stick at a rate of 100 mm/minute. The hardness corresponds to the maximum shear force exerted by the wire on the stick at 20° C., this force being measured using a DFGS2 tensile testing machine sold by the company Indelco-Chatillon. The measurement is repeated six times. The average of the six values read using the tensile testing machine mentioned above is expressed in grams. These values are thus between 3 g and 40 g, advantageously between 4 g and 20 g and preferably between 6 g and 12 g. This operation is performed on the longest length of the cross section of the stick when the stick is in the form of a cylinder of elongated cross section. This value in grams is then normalized by this longest length, or, where appropriate, by the diameter of the stick when the stick is in the form of a cylinder of circular cross section, i.e. for example 8 mm, in order to obtain a value in grams/metre.

In other words, the hardness value according to the present invention corresponds to the maximum shear force exerted by the wire measured on the stick at 20° C., divided by the longest length of the cross section of the said stick, placed in contact with the said wire 250 μm in diameter.

According to one particular embodiment, the composition according to the invention is characterized in that the shear hardness is between 500 g/m and 2500 g/m and in particular between 750 g/m and 1500 g/m.

The composition according to the invention is in the form of an emulsion, especially an emulsion comprising a fatty phase dispersed in an aqueous phase, in particular a wax-in-water emulsion.

The composition according to the invention thus comprises a continuous aqueous phase.

Aqueous Phase

The composition according to the invention comprises an aqueous phase, which may be formed essentially from water or which may comprise a mixture of water and of water-miscible or water-soluble solvent (miscibility in water of greater than 50% by weight at 25° C.), for instance lower monoalcohols containing from 1 to 5 carbon atoms, such as ethanol or isopropanol, glycols containing from 2 to 8 carbon atoms, such as propylene glycol, ethylene glycol, 1,3-butylene glycol or dipropylene glycol, $C_3$-$C_4$ ketones, $C_2$-$C_4$ aldehydes and glycerol, and mixtures thereof.

According to one embodiment, the composition comprises an aqueous phase in a content of greater than 40%, preferably greater than 45% by weight and better still greater than 50% by weight, and/or a content of less than 80% by weight, preferably less than 75% by weight, preferably ranging from 40% to 80% by weight and especially ranging from 50% to 75% by weight, relative to the total weight of the composition.

The composition according to the invention may also contain at least one emulsifier.

Emulsifiers

According to the invention, an emulsifier appropriately chosen to obtain a wax-in-water or oil-in-water emulsion is generally used. In particular, an emulsifier having at 25° C. an HLB (hydrophilic-lipophilic balance), in the Griffin sense, of greater than or equal to 8 may be used.

The HLB value according to Griffin is defined in J. Soc. Cosm. Chem. 1954 (volume 5), pages 249-256.

These emulsifiers may be chosen from nonionic, anionic, cationic and amphoteric surfactants or polymeric surfactants. Reference may be made to the document "Encyclopaedia of Chemical Technology, Kirk-Othmer", volume 22, pp. 333-432, 3rd edition, 1979, Wiley, for the definition of the properties and (emulsifying) functions of surfactants, in particular pp. 347-377 of this reference, for anionic, amphoteric and nonionic surfactants.

The surfactants preferably used in the composition according to the invention are chosen from:

a) nonionic surfactants with an HLB of greater than or equal to 8 at 25° C., used alone or as a mixture; mention may be made especially of:

saccharide esters and ethers such as the mixture of cetyl-stearyl glucoside and of cetyl and stearyl alcohols, for instance Montanov 68 from SEPPIC;

oxyethylenated and/or oxypropylenated ethers (which may comprise from 1 to 150 oxyethylene and/or oxypropylene groups) of glycerol;

oxyethylenated and/or oxypropylenated ethers (which may comprise from 1 to 150 oxyethylene and/or oxypropylene groups) of fatty alcohols (especially of $C_8$-$C_{24}$ and preferably $C_{12}$-$C_{18}$ alcohol), such as oxyethylenated cetearyl alcohol ether containing 30 oxyethylene groups (CTFA name Ceteareth-30), oxyethylenated stearyl alcohol ether containing 20 oxyethylene groups (CTFA name Steareth-20) and the oxyethylenated ether of the mixture of $C_{12}$-$C_{15}$ fatty alcohols comprising 7 oxyethylene groups (CTFA name $C_{12-15}$ Pareth-7) sold under the name Neodol 25-7® by Shell Chemicals;

fatty acid esters (especially of a $C_8$-$C_{24}$ and preferably $C_{16}$-$C_{22}$ acid) of polyethylene glycol (which may comprise from 1 to 150 ethylene glycol units), such as PEG-50 stearate and PEG-40 monostearate sold under the name Myrj 52P® by the company ICI Uniqema;

fatty acid esters (especially of a $C_8$-$C_{24}$ and preferably $C_{16}$-$C_{22}$ acid) of oxyethylenated and/or oxypropylenated glyceryl ethers (which may comprise from 1 to 150 oxyethylene and/or oxypropylene groups), for instance PEG-200 glyceryl monostearate sold under the name Simulsol 220 TM® by the company SEPPIC; glyceryl stearate polyethoxylated with 30 ethylene oxide groups, for instance the product Tagat S® sold by the company Evonik Goldschmidt, glyceryl oleate polyethoxylated with 30 ethylene oxide groups, for instance the product Tagat O® sold by the company Evonik Goldschmidt, glyceryl cocoate polyethoxylated with 30 ethylene oxide groups, for instance the product Varionic LI 13® sold by the company Sherex, glyceryl isostearate polyethoxylated with 30 ethylene oxide groups, for instance the product Tagat L® sold by the company Evonik Goldschmidt, and glyceryl laurate polyethoxylated with 30 ethylene oxide groups, for instance the product Tagat I® from the company Evonik Goldschmidt;

fatty acid esters (especially of a $C_8$-$C_{24}$ and preferably $C_{16}$-$C_{22}$ acid) of oxyethylenated and/or oxypropylenated sorbitol ethers (which may comprise from 1 to 150 oxyethylene and/or oxypropylene groups), for instance polysorbate 20 sold under the name Tween 20® by the company Croda, and polysorbate 60 sold under the name Tween 60® by the company Croda;

dimethicone copolyol, such as the product sold under the name Q2-5220® by the company Dow Corning;

dimethicone copolyol benzoate (Finsolv SLB 101® and 201® by the company Finetex);

copolymers of propylene oxide and of ethylene oxide, also known as EO/PO polycondensates;

and mixtures thereof.

The EO/PO polycondensates are more particularly copolymers consisting of polyethylene glycol and polypropylene glycol blocks, for instance polyethylene glycol/polypropylene glycol/polyethylene glycol triblock polycondensates. These triblock polycondensates have, for example, the following chemical structure:

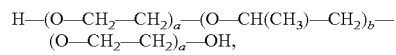

in which formula a ranges from 2 to 120 and b ranges from 1 to 100.

The EO/PO polycondensate preferably has a weight-average molecular weight ranging from 1000 to 15 000 and better still ranging from 2000 to 13 000. Advantageously, the said EO/PO polycondensate has a cloud point, at 10 g/l in distilled water, of greater than or equal to 20° C. and preferably greater than or equal to 60° C. The cloud point is measured according to ISO standard 1065. As EO/PO polycondensates that may be used according to the invention, mention may be made of the polyethylene glycol/polypropylene glycol/polyethylene glycol triblock polycondensates sold under the name Synperonic®, for instance Synperonic PE/L44® and Synperonic PE/F127®, by the company ICI.

b) nonionic surfactants with an HLB of less than 8 at 25° C., optionally combined with one or more nonionic surfactants with an HLB of greater than 8 at 25° C., such as those mentioned above; mention may be made especially of:

saccharide esters and ethers, such as sucrose stearate, sucrose cocoate and sorbitan stearate, and mixtures thereof, for instance Arlatone 2121® sold by the company ICI;

oxyethylenated and/or oxypropylenated ethers (which may comprise from 1 to 150 oxyethylene and/or oxypropylene groups) of fatty alcohols (especially of $C_8$-$C_{24}$ and preferably $C_{12}$-$C_{18}$ alcohols) such as the oxyethylenated ether of stearyl alcohol containing two oxyethylene groups (CTFA name Steareth-2);

fatty acid esters (especially of a $C_8$-$C_{24}$ and preferably $C_{16}$-$C_{22}$ acid) of polyols, especially of glycerol or of sorbitol, such as glyceryl stearate, glyceryl stearate such as the product sold under the name Tegin M® by the company Evonik Goldschmidt, glyceryl laurate such as the product sold under the name Imwitor 312® by the company Hüls, polyglyceryl-2 stearate, sorbitan tristearate or glyceryl ricinoleate;

lecithins, such as soybean lecithins (for instance Emulmetik 100 J from Cargill, or Biophilic H from Lucas Meyer);

the mixture of cyclomethicone/dimethicone copolyol sold under the name Q2-3225C® by the company Dow Corning, c) anionic surfactants such as:

salts of $C_{16}$-$C_{30}$ fatty acids, especially those derived from amines, for instance triethanolamine stearate and/or 2-amino-2-methyl-1,3-propanediol stearate. Triethanolamine stearate is generally obtained by simple mixing of stearic acid and triethanolamine;

polyoxyethylenated fatty acid salts, especially those derived from amines or alkali metal salts, and mixtures thereof;

phosphoric esters and salts thereof, such as "DEA oleth-10 phosphate" (Crodafos N 10N from the company Croda) or monocetyl monopotassium phosphate or potassium cetyl phosphate (Amphisol K from Givaudan);

sulfosuccinates such as "Disodium PEG-5 citrate lauryl sulfosuccinate" and "Disodium ricinoleamido MEA sulfosuccinate";

alkyl ether sulfates, such as sodium lauryl ether sulfate; isethionates;

acylglutamates such as "Disodium hydrogenated tallow glutamate" (Amisoft HS-21 R® sold by the company Ajinomoto) and sodium stearoyl glutamate (Amisoft HS-11 PF® sold by the company Ajinomoto), and mixtures thereof;

soybean derivatives, for instance potassium soyate;

citrates, for instance glyceryl stearate citrate (Axol C 62 Pellets from Degussa);

proline derivatives, for instance sodium palmitoyl proline (Sepicalm VG from SEPPIC) or the mixture of sodium palmitoyl sarcosinate, magnesium palmitoyl glutamate, palmitic acid and palmitoyl proline (Sepifeel One from SEPPIC);

lactylates, for instance sodium stearoyl lactylate (Akoline SL from Karlshamns AB);

sarcosinates, for instance sodium palmitoyl sarcosinate (Nikkol sarcosinate PN) or the 75/25 mixture of stearoyl sarcosine and myristoyl sarcosine (Crodasin SM from Croda);

sulfonates, for instance sodium $C_{14}$-$C_{17}$ alkyl sec sulfonate (Hostapur SAS 60 from Clariant);

glycinates, for instance sodium cocoyl glycinate (Amilite GCS-12 from Ajinomoto).

The compositions in accordance with the invention may also contain one or more amphoteric surfactants, for instance N-acylamino acids such as N-alkylaminoacetates and disodium cocoamphodiacetate, and amine oxides such as stearamine oxide, or alternatively silicone surfactants, for instance dimethicone copolyol phosphates, such as the product sold under the name Pecosil PS100® by the company Phoenix Chemical.

The emulsifier that may be used may also be a polymeric surfactant, especially a heat-induced gelling polymer.

According to one particular embodiment of the invention, the emulsifier is chosen from (i) salts of $C_{16}$-$C_{30}$ fatty acids, especially those derived from amines, for instance triethanolamine stearate; (ii) oxyethylenated and/or oxypropylenated ethers (possibly comprising from 1 to 150 oxyethylene and/or oxypropylene groups) of fatty alcohols (especially of a $C_8$-$C_{24}$ and preferably $C_{12}$-$C_{18}$ alcohol) such as the oxyethylenated ether of stearyl alcohol containing 2 oxyethylene groups (CTFA name: Steareth-2); (iii) esters of fatty acids (especially of a $C_8$-$C_{24}$ and preferably $C_{16}$-$C_{22}$ acid) and of a polyol, especially of glycerol or sorbitol, such as glyceryl stearate, such as the product sold under the name Tegin M® by the company Evonik Goldschmidt; (iv) phosphoric esters and salts thereof such as potassium cetyl phosphate (Amphisol K from Givaudan) and/or (v) esters of fatty acids (especially of $C_8$-$C_{24}$ and preferably $C_{16}$-$C_{22}$ acids) and of oxyethylenated and/or oxypropylenated ethers (possibly comprising from 1 to 150 oxyethylene and/or oxypropylene groups), for instance glyceryl stearate polyethoxylated with 30 ethylene oxide groups, for instance the product Tagat® S sold by the company Evonik Goldschmidt, and (vi) mixtures thereof.

Steareth-2, glyceryl stearate, triethanolamine stearate, glyceryl stearate polyethoxylated with 30 ethylene oxide groups, and potassium cetyl phosphate, or mixtures thereof, are even more particularly suitable as emulsifier in accordance with the invention.

According to one embodiment, the composition according to the invention comprises at least one anionic surfactant and optionally at least one nonionic surfactant, in particular a nonionic surfactant with an HLB of greater than or equal to 8 at 25° C., the said surfactants possibly being advantageously chosen from the surfactants mentioned above.

Still according to this embodiment, the composition according to the invention comprises at least one anionic surfactant chosen from salts of $C_{16}$-$C_{30}$ fatty acids, especially those derived from amines, for instance triethanolamine stearate; phosphoric esters and salts thereof, such as potassium cetyl phosphate (Amphisol K from Givaudan) and mixtures thereof and optionally at least one nonionic surfactant chosen from oxyethylenated and/or oxypropylenated ethers (possibly comprising from 1 to 150 oxyethylene and/or oxypropylene groups) of fatty alcohols (especially of $C_8$-$C_{24}$ and preferably $C_{12}$-$C_{18}$ alcohols) such as the oxyethylenated ether of stearyl alcohol containing 2 oxyethylene groups (CTFA name: Steareth-2); esters of fatty acids (especially of a $C_8$-$C_{24}$ and preferably $C_{16}$-$C_{22}$ acid) and of a polyol, especially of glycerol or sorbitol, such as glyceryl stearate, such as the product sold under the name Tegin M® by the company Evonik Goldschmidt; esters of fatty acids (especially of $C_8$-$C_{24}$ and preferably $C_{16}$-$C_{22}$ acids) and of oxyethylenated and/or oxypropylenated ethers (possibly comprising from 1 to 150 oxyethylene and/or oxypropylene groups), for instance glyceryl stearate polyethoxylated with 30 ethylene oxide groups, for instance the product Tagat® S sold by the company Evonik Goldschmidt, and mixtures thereof. According to one embodiment, the composition according to the invention comprises at least one emulsifier chosen from potassium cetyl phosphate, Steareth-2 and 20, and cetyl alcohol, and a mixture thereof. Advantageously, it is a mixture of potassium cetyl phosphate and Steareth-2.

The composition according to the invention may contain from 0.01% to 30% by weight, better still from 1% to 15% by weight and even better still from 2% to 10% by weight of emulsifier relative to the total weight of the said composition.

The composition according to the invention may also contain at least one hydrophilic gelling agent.

Hydrophilic Gelling Agent

The hydrophilic gelling agents that may be used in the compositions according to the invention may be chosen from:

homopolymers or copolymers of acrylic or methacrylic acid or the salts and esters thereof, and in particular the products sold under the names Versicol F® or Versicol K® by the company Allied Colloid, Ultrahold 8® by the company Ciba-Geigy, and the polyacrylic acids of Synthalen K® type;

copolymers of acrylic acid and of acrylamide sold in the form of the sodium salt thereof under the name Reten® by the company Hercules, sodium polymethacrylate sold under the name Darvan 7® by the company Vanderbilt, and the sodium salts of polyhydroxycarboxylic acids sold under the name Hydagen F® by the company Henkel;

polyacrylic acid/alkyl acrylate copolymers of the Pemulen® type;

AMPS (polyacrylamidomethylpropanesulfonic acid partially neutralized with ammonia and highly crosslinked) sold by the company Clariant;

AMPS/acrylamide copolymers of the SepiGel® or SimulGel® type, sold by the company SEPPIC, and AMPS/polyoxyethylenated alkyl methacrylate copolymers (crosslinked or non-crosslinked), and mixtures thereof.

The water-soluble film-forming polymers mentioned above may also act as hydrophilic gelling agents.

The hydrophilic gelling agent(s) may be present in the composition according to the invention in a solids content ranging from 0.01% to 30% by weight, preferably from 0.5% to 20% by weight and better still from 1% to 15% by weight relative to the total weight of the said composition.

Fatty Phase

The composition according to the invention comprises a fatty phase, comprising at least carnauba wax, synthetic beeswax or a mixture thereof, which may serve as texturizer(s) for the composition.

The term "texturizer" means a compound capable of giving the composition texture, especially by forming an aggregated network of particles.

Such a texturizer remains immiscible in the aqueous phase, and may be in the form of a dispersion in the said aqueous phase. Such a texturizer, when it is present in sufficient amount, thus leads to semi-solid or solid textures.

The carnauba wax and/or synthetic beeswax are present in the composition according to the invention in a content of at least 2% by weight, advantageously of at least 3% by weight, better still at least 4% by weight and especially from 2% to 30%, for example from 2% to 25% or alternatively from 2% to 10% especially when the composition comprises additional waxes, or alternatively from 15% to 25%, especially when the composition does not comprise additional waxes, or alternatively from 5% to 30% by weight relative to the total weight of the said composition.

In the context of the present invention, the term "carnauba wax and/or synthetic beeswax" means carnauba wax, synthetic beeswax or a mixture thereof.

Without the invention being bound to any theory, the inventors have put forward the hypothesis that the characteristic associated with the presence in the wax-in-water emulsion of carnauba wax and/or synthetic beeswax in a content at least 2% by weight relative to the total weight of the emulsion, combined with the removal of heat in accordance with the invention, enables a wax-in-water emulsion to achieve the hardness required for the application specifically sought in the context of the present invention, by means of a particular arrangement of wax particles. The inventors have more particularly put forward the hypothesis that this choice of waxes in this minimum required content makes it possible to obtain a particular crystal morphology, especially at least partially in the form of needles, and thus the production of a network of sufficient rigidity, allowing a trapping of water molecules that is particularly suited to the hardness requirements and suitable for obtaining good makeup properties.

In other words, the organization of the wax crystals participates fully in the structuring of the stick and clearly distinguishes the stick obtained in the context of the present invention from a conventional mascara emulsion, which is deformable and applicable using conventional applicators, for example brushes.

Carnauba Wax

Carnauba wax generally contains fatty acid esters, for example in a proportion of 80% to 85% by weight, fatty alcohols, for example in a proportion of 10% to 15% by weight, acids, for example in a proportion of 3% to 6% by weight, and hydrocarbon-based chains, for example in a proportion of 1% to 3% by weight, relative to the total weight of the wax. It may in particular contain a high content of dial ester, especially about 20% by weight relative to the total weight of the wax, hydroxylated fatty acid, especially about 6% by weight, and cinnamic acid, especially about 10% by weight, relative to the total weight of the wax.

The fatty acid esters in a proportion of 80% to 85% by weight may comprise from 36% to 40% by weight of monoesters, from 26% to 34% of diesters of cinnamic acid and from 10% to 14% by weight of hydroxy esters.

Its melting point is about 78 to 85° C.

Carnauba wax is especially sold by the company Strahl & Pitsch under the trade name Carnauba Wax SP 63®, or by the company Baerlocher under the trade name Cerauba T1.

Synthetic Beeswax

Synthetic beeswax generally contains esters of $C_{16}$ to $C_{36}$ fatty acids and fatty alcohols. Its melting point is about 50 to 60° C.

Synthetic beeswax is especially sold by the company Evonik Goldschmidt under the trade name Cyclochem® 326 A.

According to one particular embodiment, the composition may be free of additional waxes. The content of carnauba wax and/or synthetic beeswax may then be between 15% and 30% by weight, for example between 15% and 25% by weight, relative to the total weight of the composition.

The composition according to the invention may also comprise at least one additional texturing or non-texturing dispersant, which may be chosen from (i) additional waxes, other than carnauba wax and/or synthetic beeswax, (ii) semicrystalline polymers, (iii) lipophilic gelling agents, and (iv) mixtures thereof.

The additional dispersant(s) may represent from 1% to 40% by weight, preferably from 2.5% to 30% and even more preferably from 5% to 25% by weight relative to the total weight of the composition according to the invention. The amount of additional dispersant may be adjusted by a person skilled in the art as a function of the structuring properties of the said agents.

The composition according to the invention may thus also comprise at least one additional wax.

Additional Wax(es)

The additional waxes under consideration in the context of the present invention are generally deformable or non-deformable lipophilic compounds that are solid at room temperature (25° C.), with a solid/liquid reversible change of state, having a melting point of greater than or equal to 30° C., which may be up to 200° C. and in particular up to 120° C.

When a liquid fatty phase is present, by bringing one or more waxes in accordance with the invention to the liquid state (melting), it is possible to make it or them miscible with one or more oils and to form a macroscopically homogeneous wax(es)+oil(s) mixture, but on returning the temperature of the said mixture to room temperature, recrystallization of the wax(es) in the oil(s) of the mixture is obtained.

In particular, the additional waxes that are suitable for the invention may have a melting point of greater than or equal to 45° C. and in particular greater than or equal to 55° C.

For the purposes of the invention, the melting point corresponds to the temperature of the most endothermic peak observed by thermal analysis (DSC) as described in ISO standard 11357-3; 1999. The melting point of the wax may be measured using a differential scanning calorimeter (DSC), for example the calorimeter sold under the name MDSC 2920 by the company TA Instruments.

The measuring protocol is as follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation of the difference in power absorbed by the empty crucible and by the crucible containing the sample of wax is measured as a function of the temperature. The melting point of the compound is the temperature value corresponding to the top of the peak of the curve representing the variation in the difference in absorbed power as a function of the temperature.

The additional waxes that may be used in the compositions according to the invention are chosen from waxes that are solid at room temperature, of animal, plant, mineral or synthetic origin, and mixtures thereof.

Hydrocarbon-based waxes, for instance natural beeswax (or blanched beeswax), lanolin wax or Chinese insect wax; rice wax, candelilla wax, ouricury wax, esparto grass wax, cork fibre wax, sugarcane wax, Japan wax and sumach wax; montan wax, microcrystalline waxes, paraffins and ozokerite; polyethylene waxes, the waxes obtained by Fischer-Tropsch synthesis and waxy copolymers, and also esters thereof, may especially be used.

Mention may also be made of waxes obtained by catalytic hydrogenation of animal or plant oils containing linear or branched $C_8$-$C_{32}$ fatty chains.

Among these waxes that may especially be mentioned are hydrogenated jojoba oil, hydrogenated sunflower oil, hydrogenated castor oil, hydrogenated coconut oil, hydrogenated lanolin oil and bis(1,1,1-trimethylolpropane) tetrastearate sold under the name Hest 2T-4S by the company Heterene, bis(1,1,1-trimethylolpropane) tetrabehenate sold under the name Hest 2T-4B by the company Heterene.

Mention may also be made of silicone waxes, for instance alkyl or alkoxy dimethicones containing from 16 to 45 carbon atoms, and fluoro waxes.

The wax obtained by hydrogenation of olive oil esterified with stearyl alcohol, sold under the name Phytowax Olive 18L57 or else the waxes obtained by hydrogenation of castor oil esterified with cetyl alcohol sold under the names Phytowax ricin 16L64 and 22L73 by the company Sophim may also be used. Such waxes are described in patent application FR-A-2 792 190.

According to one particular embodiment, the compositions in accordance with the invention may comprise at least one "tacky" wax, i.e. a wax with a tack of greater than or equal to 0.7 N.s and a hardness of less than or equal to 3.5 MPa.

The use of a tacky wax may especially allow the production of a cosmetic composition that is easy to apply to the eyelashes, that attaches well to the eyelashes and that leads to the formation of a smooth, uniform and thickening makeup.

The tacky wax used may especially have a tack ranging from 0.7 N.s to 30 N.s, in particular greater than or equal to 1 N.s, especially ranging from 1 N.s to 20 N.s, in particular greater than or equal to 2 N.s, especially ranging from 2 N.s to 10 N.s and in particular ranging from 2 N.s to 5 N.s.

The tack of the wax is determined by measuring the change in force (compression force or stretching force) as a function of time, at 20° C., using the texturometer sold under the name TA-TX2i® by the company Rhea, equipped with a conical acrylic polymer spindle forming an angle of 45°.

The measuring protocol is as follows:

The wax is melted at a temperature equal to the melting point of the wax+10° C. The molten wax is poured into a container 25 mm in diameter and 20 mm deep. The wax is recrystallized at room temperature (25° C.) for 24 hours such that the surface of the wax is flat and smooth, and the wax is then stored for at least 1 hour at 20° C. before measuring the tack.

The texturometer spindle is displaced at a speed of 0.5 mm/s then penetrates the wax to a penetration depth of 2 mm. When the spindle has penetrated the wax to a depth of 2 mm, the spindle is held still for 1 second (corresponding to the relaxation time) and is then withdrawn at a speed of 0.5 mm/s.

During the relaxation time, the force (compression force) decreases greatly until it becomes zero, and then, during the withdrawal of the spindle, the force (stretching force) becomes negative and then rises again to the value 0. The tack corresponds to the integral of the curve of the force as a function of time for the part of the curve corresponding to negative values of the force (stretching force). The tack value is expressed in N.s.

The tacky wax that may be used generally has a hardness of less than or equal to 3.5 MPa, in particular ranging from 0.01 MPa to 3.5 MPa, especially ranging from 0.05 MPa to 3 MPa or even ranging from 0.1 MPa to 2.5 MPa.

The hardness of the tacky wax is determined by measuring the compression force, which is measured at 20° C. using the texturometer sold under the name TA-XT2 by the company Rheo, equipped with a stainless-steel cylinder 2 mm in diameter travelling at a measuring speed of 0.1 mm/s, and penetrating the wax to a penetration depth of 0.3 mm.

The measuring protocol is as follows:

The wax is melted at a temperature equal to the melting point of the wax+10° C. The molten wax is cast in a container 25 mm in diameter and 20 mm deep. The wax is recrystallized at room temperature (25° C.) for 24 hours such that the surface of the wax is flat and smooth, and the wax is then kept for at least 1 hour at 20° C. before performing measuring the hardness or the tack.

The texturometer spindle is displaced at a speed of 0.1 mm/s, and then penetrates the wax to a penetration depth of 0.3 mm. When the spindle has penetrated the wax to a depth of 0.3 mm, the spindle is held steady for 1 second (corresponding to the relaxation time) and is then removed at a speed of 0.5 mm/s.

The hardness value is the maximum compression force measured divided by the area of the texturometer or cylinder in contact with the wax.

Tacky waxes that may be used include a $C_{20}$-$C_{40}$ alkyl (hydroxystearyloxy)stearate (the alkyl group containing from 20 to 40 carbon atoms), alone or in a mixture, in particular a $C_{20}$-$C_{40}$ alkyl 12-(12'-hydroxystearyloxy)stearate, of formula (II):

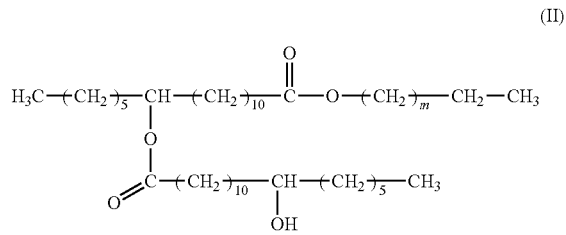

(II)

in which m is an integer ranging from 18 to 38, or a mixture of compounds of formula (II).

Such a wax is especially sold under the names "Kester Wax K 82 P®" and "Kester Wax K 80 P®" by the company Koster Keunen.

It is also possible to use a microcrystalline wax sold under the reference SP18 by the company Strahl & Pitsch, which has a hardness of about 0.46 MPa and a tack value of about 1 N.s.

The wax(es) may be present in the form of an aqueous wax microdispersion. The expression "aqueous wax microdispersion" means an aqueous dispersion of wax particles in which the size of the said wax particles is less than or equal to about 1 μm.

Wax microdispersions are stable dispersions of colloidal wax particles, and are described especially in "Microemulsions Theory and Practice", L. M. Prince Ed., Academic Press (1977) pages 21-32.

In particular, these wax microdispersions may be obtained by melting the wax in the presence of a surfactant, and optionally of a portion of water, followed by gradual addition of hot water with stirring. The intermediate formation of an emulsion of the water-in-oil type is observed, followed by a phase inversion, with final production of a microemulsion of the oil-in-water type. On cooling, a stable microdispersion of solid wax colloidal particles is obtained.

The wax microdispersions may also be obtained by stirring the mixture of wax, surfactant and water using stirring means such as ultrasound, high-pressure homogenizers or turbomixers.

The particles of the wax microdispersion preferably have mean sizes of less than 1 µm (especially ranging from 0.02 µm to 0.99 µm) and preferably less than 0.5 µm (especially ranging from 0.06 µm to 0.5 µm).

These particles consist essentially of a wax or a mixture of waxes. However, they may comprise a small proportion of oily and/or pasty fatty additives, a surfactant and/or a common liposoluble additive/active agent.

According to one embodiment, the composition also comprises at least one additional wax, other than synthetic beeswax and carnauba wax, chosen from waxes that are solid at room temperature, optionally in the form of an aqueous wax microdispersion, of animal, plant, mineral or synthetic origin, and mixtures thereof. Still according to this embodiment, at least one additional wax may have a melting point of greater than or equal to 45° C., in particular greater than or equal to 55° C., and/or may have a tack of greater than or equal to 0.7 N.s and a hardness of less than or equal to 3.5 MPa.

According to one particular embodiment, the composition according to the invention may comprise as additional wax at least ozokerite. Specifically, the inventors have found that the presence of ozokerite is advantageous since it gives the walls of the article containing it a non-stick property. In other words, its presence makes it possible to avoid jamming of the stick on cooling, by avoiding excessive adherence of the stick to the walls of the conditioning article, and, what is more, is favourable towards giving the stick a smooth and glossy surface.

According to this embodiment, the composition according to the invention may comprise from 5% to 25% by weight and in particular from 10% to 20% by weight of ozokerite, relative to the total weight of the composition.

The composition according to the invention may have a total content of wax(es), i.e. of carnauba wax and/or synthetic wax and of additional wax(es), of between 2% and 35% by weight and preferably between 5% and 30% by weight relative to the total weight of the said composition.

The composition according to the invention may also comprise at least one semi-crystalline polymer.

Semi-Crystalline Polymers

The term "semi-crystalline polymer" means polymers comprising a crystallizable portion, a crystallizable side chain or a crystallizable block in the backbone, and an amorphous portion in the backbone and also having a first-order reversible phase-change temperature, in particular of melting (solid-liquid transition). When the crystallizable portion is in the form of a crystallizable block of the polymer backbone, the amorphous portion of the polymer is in the form of an amorphous block. In this case, the semi-crystalline polymer is a block copolymer, for example, of the diblock, triblock or multiblock type, comprising at least one crystallizable block and at least one amorphous block. The term "block" generally means at least five identical repeating units. The crystallizable block(s) is (are) of chemical nature different than that of the amorphous block(s).

The semi-crystalline polymer has a melting point of greater than or equal to 30° C., especially ranging from 30° C. to 80° C., preferably ranging from 30° C. to 60° C. This melting point is a first-order change of state temperature.

This melting point may be measured by any known method and in particular using a differential scanning calorimeter (DSC).

Advantageously, the semi-crystalline polymer(s) to which the invention applies have a number-average molecular mass of greater than or equal to 1000. Advantageously, the semi-crystalline polymer(s) of the composition in accordance with the invention have a number-average molecular mass $\overline{M}n$ ranging from 2000 to 800 000, preferably from 3000 to 500 000, better still from 4000 to 150 000, especially less than 100 000 and better still from 4000 to 99 000. Preferably, they have a number-average molecular mass of greater than 5600, for example ranging from 5700 to 99 000. For the purposes of the invention, the term "crystallizable chain or block" means a chain or block which, if it were alone, would reversibly change from the amorphous state to the crystalline state, depending on whether the system is above or below the melting point. For the purposes of the invention, a chain is a group of atoms, which is pendent or lateral relative to the polymer backbone. A block is a group of atoms belonging to the backbone, this group constituting one of the repeating units of the polymer. Advantageously, the "crystallizable side chain" may be a chain containing at least six carbon atoms.

The semi-crystalline polymer may be chosen from block copolymers comprising at least one crystallizable block and at least one amorphous block, and homopolymers and copolymers bearing at least one crystallizable side chain per repeating unit, and mixtures thereof.

Such polymers are described, for example, in document EP 1 396 259.

According to a more particular embodiment of the invention, the polymer is derived from a monomer containing a crystallizable chain chosen from saturated $C_{14}$-$C_{22}$ alkyl (meth)acrylates.

As a particular example of a structuring semi-crystalline polymer that may be used in the composition in accordance with the invention, mention may be made of the Intelimer® products from the company Landec described in the brochure "Intelimer® Polymers", Landec IP22 (Rev. 4-97).

These polymers are in solid form at room temperature (25° C.). They bear crystallizable side chains.

The semi-crystalline polymer(s) may be present in a content ranging from 0.1% to 30% by weight relative to the total weight of the composition.

The composition according to the invention may also comprise at least one lipophilic gelling agent.

Lipophilic Gelling Agents

The gelling agents that may be used in the compositions according to the invention may be organic or mineral, polymeric or molecular lipophilic gelling agents.

Mineral lipophilic gelling agents that may be mentioned include optionally modified clays, for instance hectorites modified with a $C_{10}$ to $C_{22}$ ammonium chloride, for instance hectorite modified with distearyldimethylammonium chloride, for instance the product sold under the name Bentone 38V® by the company Elementis.

Mention may also be made of fumed silica optionally subjected to a hydrophobic surface treatment, the particle size of which is less than 1 µm. Specifically, it is possible to chemically modify the surface of the silica, by chemical reaction generating a reduced number of silanol groups present at the surface of the silica. It is especially possible to substitute silanol groups with hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as "silica silylate" according to the CTFA (6th edition, 1995). They are sold, for example, under the references Aerosil R812® by the company Degussa, and Cab-O-Sil TS-530® by the company Cabot;

dimethylsilyloxyl or polydimethylsiloxane groups, which are obtained especially by treating fumed silica in the presence of polydimethylsiloxane or dimethyl-dichlorosilane. Silicas thus treated are known as "silica dimethyl silylate" according to the CTFA (6th edition, 1995). They are sold, for example, under the references Aerosil R972® and Aerosil R974® by the company Degussa, and Cab-O-Sil TS-610® and Cab-O-Sil TS-720® by the company Cabot.

The hydrophobic fumed silica in particular has a particle size that may be nanometric to micrometric, for example ranging from about 5 to 200 nm.

It is also possible to use non-polymeric molecular organic gelling agents, also known as organo-gelling agents, combined with a liquid fatty phase (which may be the liquid fatty phase of the composition according to the invention), which are compounds whose molecules are capable of establishing physical interactions between themselves, leading to self-aggregation of the molecules with formation of a supramolecular 3-D network that is responsible for the gelling of the liquid fatty phase.

The supramolecular network may result from the formation of a network of fibrils (caused by the stacking or aggregation of organogelling molecules), which immobilizes the molecules of the liquid fatty phase.

The ability to form this network of fibrils, and thus to gel, depends on the nature (or chemical class) of the organogelling agent, on the nature of the substituents borne by its molecules for a given chemical class, and on the nature of the liquid fatty phase.

The physical interactions are of diverse nature but exclude co-crystallization. These physical interactions are in particular interactions of self-complementary hydrogen interaction type, π interactions between unsaturated rings, dipolar interactions, coordination bonds with organometallic derivatives, and combinations thereof. In general, each molecule of an organogelling agent can establish several types of physical interaction with a neighbouring molecule. Thus, advantageously, the molecules of the organogelling agents according to the invention comprise at least one group capable of establishing hydrogen bonds and better still at least two groups, at least one aromatic ring and better still at least two aromatic rings, at least one or more ethylenically unsaturated bonds and/or at least one or more asymmetric carbons. Preferably, the groups capable of forming hydrogen bonds are chosen from hydroxyl, carbonyl, amine, carboxylic acid, amide, urea and benzyl groups, and combinations thereof.

The organogelling agent(s) according to the invention is (are) soluble in the liquid fatty phase after heating to obtain a transparent uniform liquid phase. They may be solid or liquid at room temperature (25° C.) and atmospheric pressure.

The molecular organogelling agent(s) that may be used in the composition according to the invention is (are) especially those described in the document "Specialist Surfactants" edited by D. Robb, 1997, pp. 209-263, Chapter 8 by P. Terech, European patent applications EP-A-1 068 854 and EP-A-1 086 945, or alternatively in patent application WO-A-02/47031.

Mention may be made especially, among these organogelling agents, of amides of carboxylic acids, in particular of tricarboxylic acids, for instance cyclohexanetricarboxamides (see European patent application EP-A-1 068 854), diamides with hydrocarbon-based chains each containing from 1 to 22 carbon atoms, for example from 6 to 18 carbon atoms, the said chains being unsubstituted or substituted with at least one substituent chosen from ester, urea and fluoro groups (see patent application EP-A-1 086 945) and especially diamides resulting from the reaction of diamino-cyclohexane, in particular diaminocyclohexane in trans form, and of an acid chloride, for instance N,N'-bis(dodecanoyl)-1,2-diaminocyclohexane, N-acylamino acid amides, for instance the diamides resulting from the action of an N-acylamino acid with amines containing from 1 to 22 carbon atoms, for instance those described in document WO-93123008 and especially N-acylglutamic acid amides in which the acyl group represents a $C_8$ to $C_{22}$ alkyl chain, such as N-lauroyl-L-glutamic acid dibutylamide, manufactured or sold by the company Ajinomoto under the name GP-1, and mixtures thereof.

The polymeric organic lipophilic gelling agents are, for example:

partially or totally crosslinked elastomeric organopolysiloxanes of three-dimensional structure, for instance those sold under the names KSG6®, KSG16® and KSG18® from Shin-Etsu, Trefil E-505C® or Trefil E-506C® from Dow Corning, Gransil SR-CYC®, SR DMF 10®, SR-DC556®, SR 5CYC Gel®, SR DMF 10 Gel® and SR DC 556 Gel® from Grant Industries and SF 1204® and JK 113® from General Electric;

ethylcellulose, for instance the product sold under the name Ethocel® by Dow Chemical;

polycondensates of polyamide type resulting from condensation between (α) at least one acid chosen from dicarboxylic acids containing at least 32 carbon atoms, such as fatty acid dimers, and (β) an alkylenediamine and in particular ethylenediamine, in which the polyamide polymer comprises at least one carboxylic acid end group esterified or amidated with at least one saturated and linear monoalcohol or one saturated and linear monoamine containing from 12 to 30 carbon atoms, and in particular ethylenediamine/stearyl dilinoleate copolymers such as the product sold under the name Uniclear 100 VG® by the company Arizona Chemical;

silicone polyamides of polyorganosiloxane type such as those described in documents U.S. Pat. Nos. 5,874,069, 5,919,441, 6,051,216 and 5,981,680, for instance those sold under the reference Dow Corning 2-8179 Gellant® by the company Dow Corning;

galactomannans comprising from one to six and in particular from two to four hydroxyl groups per saccharide, substituted with a saturated or unsaturated alkyl chain, for instance guar gum alkylated with $C_1$ to $C_6$ and in particular $C_1$ to $C_3$ alkyl chains, and mixtures thereof;

block copolymers, optionally hydrogenated, of "diblock", "triblock" or "radial" type, in particular containing styrene blocks and ethylene/$C_3$-$C_4$ alkylene blocks. Diblock copolymers, which are preferably hydrogenated, that may be mentioned include styrene-ethylene/propylene copolymers, styrene-ethylene/butadiene copolymers and styrene-ethyl-ene/butylene copolymers. Diblock copolymers are especially sold under the name Kraton® G1701E by the company Kraton Polymers.

Triblock copolymers, which are preferably hydrogenated, that may be mentioned include styrene-ethylene/propylene-styrene copolymers, styrene-ethylene/butadiene-styrene copolymers, styrene-isoprene-styrene copolymers and styrene-butadiene-styrene copolymers. Triblock polymers are especially sold under the names Kraton® G1650, Kraton® G1652, Kraton® D1101, Kraton® D1102 and Kraton® D1160 by the company Kraton Polymers.

It is also possible to use a mixture of hydrogenated styrene-butylene/ethylene-styrene triblock copolymer and of hydrogenated ethylene-propylene-styrene star polymer, such a mixture being especially in isododecane. Such mixtures are sold, for example, by the company Penreco under the trade names VersaGel® M5960 and VersaGel® M5670.

Mention may also be made of polystyrene/polyisoprene or polystyrene/polybutadiene copolymers such as those sold under the name Luvitol HSB® by the company BASF.

Among the lipophilic gelling agents that may be used in the compositions according to the invention, mention may also be made of fatty acid esters of dextrin, such as dextrin palmitates, especially the products sold under the name Rheopearl TL® or Rheopearl KL® by the company Chiba Flour.

The lipophilic gelling agent(s) may be present in a content ranging from 0.1% to 30% by weight relative to the total weight of the composition.

The composition according to the invention may also comprise at least one pasty compound.

Pasty Compounds

For the purposes of the present invention, the term "pasty" is intended to denote a lipophilic fatty compound that undergoes a reversible solid/liquid change of state and that comprises, at a temperature of 23° C., a liquid fraction and a solid fraction. In other words, the starting melting point of the pasty compound is less than 23° C. The pasty compound is said to be in the solid state when all of its mass is in solid form and the pasty compound is said to be in the liquid state when all of its mass is in liquid form.

The liquid fraction of the pasty compound measured at 23° C. represents from 23% to 97% by weight of the compound and preferably between 25% and 85% by weight of the compound.

The liquid fraction by weight of the pasty compound at 23° C. is equal to the ratio of the heat of fusion consumed at 23° C. to the heat of fusion of the pasty compound.

The heat of fusion of the pasty compound is the amount of energy required, consumed by the compound, to change from the solid state to the liquid state. It is expressed in J/g.

The heat of fusion of the pasty compound is equal to the area under the curve of the thermogram obtained using a differential scanning calorimeter (DSC), such as the calorimeter sold under the name MDSC 2920 by the company TA Instrument, with a temperature rise of 5 or 10° C. per minute, according to standard ISO 11357-3:1999.

The heat of fusion consumed at 23° C. is the amount of energy absorbed by the sample to change from the solid state to the state that it has at 23° C., consisting of a liquid fraction and a solid fraction.

The liquid fraction of the pasty compound, measured at 32° C., preferably represents from 40% to 100% by weight of the compound and preferably from 50% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same manner as the heat of fusion consumed at 23° C.

The pasty compound is preferably chosen from synthetic compounds and compounds of plant origin. A pasty compound may be obtained by synthesis from starting materials of plant origin.

The pasty compound is advantageously chosen from:
lanolin and derivatives thereof,
polymer or non-polymer silicone compounds,
polymer or non-polymer fluoro compounds,
vinyl polymers, especially:
  olefin homopolymers
  olefin copolymers
  hydrogenated diene homopolymers and copolymers
  linear or branched oligomers, which are homopolymers or copolymers of alkyl (meth)acrylates preferably containing a $C_8$-$C_{30}$ alkyl group
  homopolymeric and copolymeric oligomers of vinyl esters containing $C_8$-$C_{30}$ alkyl groups
  homopolymeric and copolymeric oligomers of vinyl ethers containing $C_8$-$C_{30}$ alkyl groups,
  liposoluble polyethers resulting from the polyetherification between one or more $C_2$-$C_{100}$ and preferably $C_2$-$C_{50}$ diols,
  esters and polyesters,
  and mixtures thereof.

The pasty compound is preferably a polymer and especially a hydrocarbon-based polymer.

A preferred silicone and fluoro pasty compound is polymethyl trifluoropropyl methylalkyl dimethylsiloxane, manufactured under the name X22-1088 by Shin-Etsu.

When the pasty compound is a silicone and/or fluoro polymer, the composition advantageously comprises a compatibilizer such as short-chain esters, for instance isodecyl neopentanoate.

Among the liposoluble polyethers that that may especially be mentioned are copolymers of ethylene oxide and/or of propylene oxide with $C_6$-$C_{30}$ long-chain alkylene oxides, more preferably such that the weight ratio of the ethylene oxide and/or of the propylene oxide to the alkylene oxides in the copolymer is from 5:95 to 70:30. In this family, mention will be made especially of copolymers such as long-chain alkylene oxides arranged in blocks with a molecular weight of from 1000 to 10 000, for example a polyoxyethylene/polydodecylene glycol block copolymer such as the ethers of dodecanediol (22 mol) and of polyethylene glycol (45 OE) sold under the brand name Elfacos ST9 by Akzo Nobel, Among the esters that are especially preferred are:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid and 12-hydroxystearic acid, for instance those sold under the brand name Softisan 649® by the company Sasol,
phytosterol esters,
pentaerythritol esters,
esters formed from:
  at least one alcohol, at least one of the alcohols being a Guerbet alcohol, and
  a diacid dimer formed from at least one unsaturated fatty acid, for instance the ester of fatty acid dimer of tall oil containing 36 carbon atoms and of a mixture i) of Guerbet alcohols containing 32 carbon atoms and ii) of behenyl alcohol; the ester of linoleic acid dimer and of a mixture of two Guerbet alcohols, 2-tetradecyloctadecanol (32 carbon atoms) and 2-hexadecyle-icosanol (36 carbon atoms), non-crosslinked polyesters resulting from polycondensation between a linear or branched $C_4$-$C_{50}$ dicarboxylic acid or polycarboxylic acid and a $C_2$-$C_{50}$ diol or polyol, polyesters resulting from the esterification, with a polycarboxylic acid, of an aliphatic hydroxycarboxylic acid ester, for instance Risocast DA-L and Risocast DA-H sold by the Japanese company Kokyu Alcohol Kogyo, which are esters resulting from the esterification reaction of hydrogenated castor oil with dilinoleic acid or isostearic acid, aliphatic esters of an ester resulting from the esterification of an aliphatic hydroxycarboxylic acid ester with an aliphatic carboxylic acid; (Salacos HCIS (V)-L sold by the company Nisshin Oil).

The aliphatic carboxylic acid contains from 4 to 30 and preferably from 8 to 30 carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof.

The aliphatic carboxylic acid is preferably branched.

The aliphatic hydroxycarboxylic acid ester is advantageously derived from a hydroxylated aliphatic carboxylic acid containing from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups. The aliphatic hydroxycarboxylic acid ester is chosen from:

a) partial or total esters of saturated linear monohydroxylated aliphatic monocarboxylic acids;

b) partial or total esters of unsaturated monohydroxylated aliphatic monocarboxylic acids;

c) partial or total esters of saturated monohydroxylated aliphatic polycarboxylic acids;

d) partial or total esters of saturated polyhydroxylated aliphatic polycarboxylic acids;

e) partial or total esters of $C_2$ to $C_{16}$ aliphatic polyols that have reacted with a monohydroxylated or polyhydroxylated aliphatic monocarboxylic or polycarboxylic acid, and mixtures thereof.

The aliphatic esters of an ester are advantageously chosen from:

the ester resulting from the esterification reaction of hydrogenated castor oil with isostearic acid in proportions of 1 to 1 (1/1) or hydrogenated castor oil monoisostearate, the ester resulting from the esterification reaction of hydrogenated castor oil with isostearic acid in proportions of 1 to 2 (1/2) or hydrogenated castor oil diisostearate, the ester resulting from the esterification reaction of hydrogenated castor oil with isostearic acid in proportions of 1 to 3 (1/3) or hydrogenated castor oil triisostearate, and mixtures thereof.

Preferably, the pasty compound is chosen from compounds of plant origin.

Among these compounds, mention may be made especially of isomerized jojoba oil such as the trans-isomerized partially hydrogenated jojoba oil manufactured or sold by the company Desert Whale under the commercial reference Iso-Jojoba-50®, orange wax, for instance the product sold under the reference Orange Peel Wax® by the company Koster Keunen, shea butter, partially hydrogenated olive oil, for instance the product sold under the reference Beurrolive® by the company Soliance, cocoa butter, and mango oil, for instance Lipex® 302 from the company Aarhuskarlshamn.

The pasty compound may represent from 0.5% to 20% and better still 1% to 15% by weight relative to the total weight of the composition.

Liquid Fatty Phase

The composition according to the invention may comprise a liquid fatty phase. For the purposes of the patent application, the term "liquid fatty phase" means a fatty phase that is liquid at room temperature (25° C.) and atmospheric pressure (760 mmHg), composed of one or more mutually compatible non-aqueous fatty substances that are liquid at room temperature. These fatty substances are also known as oils.

The oil may be chosen from volatile oils and non-volatile oils, and mixtures thereof.

For the purposes of the invention, the term "volatile oil" means an oil that is capable of evaporating on contact with the skin or the keratin fibre in less than one hour, at room temperature and atmospheric pressure. The volatile oil(s) of the invention is (are) volatile organic solvents and/or volatile cosmetic oils, which are liquid at room temperature and which have a non-zero vapour pressure at room temperature and atmospheric pressure, in particular ranging from 0.13 Pa to 40 000 Pa (i.e. from $10^{-3}$ to 300 mmHg), in particular ranging from 1.3 Pa to 13 000 Pa (i.e. from 0.01 to 100 mmHg) and more particularly ranging from 1.3 Pa to 1300 Pa (i.e. from 0.01 to 10 mmHg).

In contrast, the term "non-volatile oil" means an oil that remains on the skin or the keratin fibre at room temperature and atmospheric pressure for at least one hour and that especially has a vapour pressure of less than $10^{-3}$ mmHg, i.e. less than 0.13 Pa.

These oils may be hydrocarbon-based oils, silicone oils or fluoro oils, or mixtures thereof.

The term "hydrocarbon-based oil" means an oil mainly containing hydrogen and carbon atoms, and possibly oxygen, nitrogen, sulfur and/or phosphorus atoms.

As examples of oils that may be used in the invention, mention may be made of:

hydrocarbon-based oils of animal origin, such as perhydrosqualene;

hydrocarbon-based plant oils such as liquid triglycerides of fatty acids of from 4 to 24 carbon atoms, for instance heptanoic or octanoic acid triglyceride, or alternatively sunflower oil, corn oil, soybean oil, marrow oil, grapeseed oil, sesame seed oil, hazelnut oil, apricot oil, macadamia oil, castor oil, avocado oil, caprylic/capric acid triglycerides, for instance those sold by the company Stearineries Dubois or those sold under the names Miglyol 810, 812 and 818 by the company Dynamit Nobel, jojoba oil and shea butter oil;

linear or branched hydrocarbons of mineral or synthetic origin, such as liquid paraffin and derivatives thereof, petroleum jelly, polydecenes, polybutenes and hydrogenated polyisobutene such as Parleam, hydrocarbon-based oils containing from 8 to 16 carbon atoms, and especially branched $C_8$-$C_{16}$ alkanes, for instance $C_8$-$C_{16}$ isoalkanes of petroleum origin (also known as isoparaffins), for instance isododecane (also known as 2,2,4,4, 6-pentamethylheptane), isodecane and isohexadecane, for example the oils sold under the trade names Isopar® or Permethyl®, or alternatively petroleum distillates, especially those sold under the name Shell Solt by the company Shell;

synthetic esters and ethers, especially of fatty acids, for instance the oils of formula $R_1COOR_2$ in which $R_1$ represents a higher fatty acid residue containing from 1 to 40 carbon atoms and $R_2$ represents a hydrocarbon-based chain containing from 1 to 40 carbon atoms with $R_1+R_2 \geq 10$, for instance purcellin oil, isononyl isononanoate, isopropyl myristate, 2-ethylhexyl palmitate, 2-octyldodecyl stearate, 2-octyldodecyl erucate, isostearyl isostearate or tridecyl trimellitate; hydroxylated esters, for instance isostearyl lactate, octyl hydroxystearate, octyldodecyl hydroxystearate, diisostearyl malate, triisocetyl citrate and fatty alkyl heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate;

fatty alcohols containing from 12 to 26 carbon atoms, for instance octyldodecanol, 2-butyloctanol, 2-hexyldecanol, 2-undecylpentadecanol or oleyl alcohol;

fluoro oils, optionally partially hydrocarbon-based and/or silicone-based;

silicone oils, for instance volatile or non-volatile, linear or cyclic polydimethylsiloxanes (PDMSs); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes or 2-phenyl ethyl trimethyl siloxysilicates, mixtures thereof.

Preferably, the oil has a molecular mass of greater than or equal to 250 g/mol, especially between 250 and 10 000 g/mol, preferably greater than or equal to 300 g/mol, especially between 300 and 8000 g/mol, and better still greater than or equal to 400 g/mol, especially between 400 and 5000 g/mol.

This oil may be chosen from:

polybutylenes such as Indopol H-100 (molar mass or MM=965 g/mol), Indopol H-300 (MM=1340 g/mol) and Indopol H-1500 (MM=2160 g/mol), sold or manufactured by the company Amoco, hydrogenated polyisobutylenes such as Panalane H-300 E sold or manufactured by the company Amoco (M=1340 g/mol), Viseal 20 000 sold or manufactured by the company Synteal (MM=6000 g/mol) and Rewopal PIB 1000 sold or manufactured by the company Witco (MM=1000 g/mol), polydecenes and hydrogenated polydecenes such as: Puresyn 10 (MM=723 g/mol) and Puresyn 150 (MM=9200 g/mol), sold or manufactured by the company Mobil Chemicals, esters such as:

linear fatty acid esters with a total carbon number ranging from 30 to 70, for instance pentaerythrityl tetrapelargonate (MM=697.05 g/mol), hydroxylated esters such as diisostearyl malate (MM=639 g/mol), aromatic esters such as tridecyl trimellitate (MM=757.19 g/mol), esters of branched C24-C28 fatty alcohol or fatty acids, such as those described in patent application EP-A-0 955 039, and in particular triisocetyl citrate (MM=865 g/mol), pentaerythrityl tetraisononanoate (MM=697.05 g/mol), glyceryl triisostearate (MM=891.51 g/mol), glyceryl tris(2-decyl)tetradecanoate (MM=1143.98 g/mol), pentaery-thrityl tetraisostearate (MM=1202.02 g/mol), polyglyceryl-2 tetraisostearate (MM=1232.04 g/mol) or pentaerythrityl tetrakis(2-decyl)tetradecanoate (MM=1538.66 g/mol), oils of plant origin such as sesame oil (820.6 g/mol), and mixtures thereof.

According to one particular embodiment, the composition is free of liquid fatty phase. In the context of the present invention, the term "free of liquid fatty phase" means that the composition comprises less than 5% and preferably less than 1% of liquid fatty phase.

The composition according to the invention may furthermore comprise at least one film-forming polymer, chosen especially from radical-mediated film-forming polymers, film-forming polycondensates and film-forming polymers of natural origin, and mixtures thereof.

Film-Forming Polymers

In the present invention, the term "film-forming polymer" means a polymer that is capable of forming, by itself or in the presence of an auxiliary film-forming agent, a macroscopically continuous film that adheres to the eyelashes, preferably a cohesive film and better still a film whose cohesion and mechanical properties are such that the said film can be isolated and manipulated in isolation, for example when the said film is prepared by pouring onto a non-stick surface such as a Teflon-coated or silicone-coated surface.

Among the film-forming polymers that may be used in the composition of the present invention, mention may be made of synthetic polymers, of free-radical type or of polycondensate type, and polymers of natural origin, and mixtures thereof.

The film-forming polymer(s) may be present in the composition according to the invention in a solids content ranging from 0.1% to 30% by weight, preferably from 0.5% to 20% by weight and better still from 1% to 15% by weight relative to the total solids content of the said composition.

The composition according to the invention may also comprise at least one radical-mediated film-forming polymer.

Radical-Mediated Film Forming Polymers

The expression "radical-mediated film forming polymer" means a polymer obtained by polymerization of monomers containing unsaturation, in particular ethylenic unsaturation, each monomer being capable of homopolymerizing (unlike polycondensates).

The film-forming polymers of radical-mediated type may be, in particular, vinyl polymers or copolymers, in particular acrylic polymers.

The vinyl film-forming polymers can result from the polymerization of monomers containing ethylenic unsaturation and containing at least one acidic group and/or esters of these acidic monomers and/or amides of these acidic monomers.

Monomers bearing an acid group which may be used are $\alpha,\beta$-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously chosen from (meth)acrylic acid esters (also known as (meth)acrylates), especially (meth)acrylates of an alkyl, in particular of a $C_1$-$C_{30}$ and preferably $C_1$-$C_{20}$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl.

Among the alkyl (meth)acrylates that may be mentioned are methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates that may be mentioned are hydroxyethyl acrylate, 2-hydroxypropyl acrylate, hydroxyethyl methacrylate and 2-hydroxypropyl methacrylate.

Among the aryl (meth)acrylates that may be mentioned are benzyl acrylate and phenyl acrylate.

The (meth)acrylic acid esters that are particularly preferred are the alkyl (meth)acrylates.

According to the present invention, the alkyl group of the esters may be either fluorinated or perfluorinated, i.e. some or all of the hydrogen atoms of the alkyl group are substituted with fluorine atoms.

Examples of amides of the acid monomers that may be mentioned are (meth)acrylamides, and especially N-alkyl (meth)acrylamides, in particular of a $C_2$-$C_{12}$ alkyl. Among the N-alkyl(meth)acrylamides that may be mentioned are N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. In particular, these monomers may be polymerized with acid monomers and/or esters thereof and/or amides thereof, such as those mentioned above.

Examples of vinyl esters that may be mentioned are vinyl acetate, vinyl neodecanoate, vinyl pivalate, vinyl benzoate and vinyl t-butylbenzoate.

Styrene monomers that may be mentioned are styrene and α-methylstyrene.

The composition according to the invention may also comprise at least one film-forming polycondensate.

Film Forming Polycondensates

Among the film-forming polycondensates that may be mentioned are polyurethanes, polyesters, polyesteramides, polyamides, epoxyester resins and polyureas.

The polyurethanes may be chosen from anionic, cationic, nonionic or amphoteric polyurethanes, polyurethane-acrylics, polyurethane-polyvinylpyrrolidones, polyester-polyurethanes, polyether-polyurethanes, polyureas and polyurea-polyurethanes, and mixtures thereof.

The polyesters may be obtained, in a known manner, by polycondensation of dicarboxylic acids with polyols, in particular diols.

The dicarboxylic acid may be aliphatic, alicyclic or aromatic. Examples of such acids that may be mentioned are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid or 2,6-naphthalenedicarboxylic acid. These dicarboxylic acid monomers may be used alone or as a combination of at least two dicarboxylic acid monomers. Among these monomers, the ones preferentially chosen are phthalic acid, isophthalic acid and terephthalic acid.

The diol may be chosen from aliphatic, alicyclic and aromatic diols. The diol used is preferably chosen from: ethylene glycol, diethylene glycol, triethylene glycol, 1,3-propanediol, cyclohexanedimethanol and 4-butanediol. Other polyols that may be used are glycerol, pentaerythritol, sorbitol and trimethylolpropane.

The polyesteramides may be obtained in a manner analogous to that of the polyesters, by polycondensation of diacids with diamines or amino alcohols. Diamines that may be used are ethylenediamine, hexamethylenediamine and meta- or para-phenylenediamine. An amino alcohol that may be used is monoethanolamine.

The polyester may also comprise at least one monomer bearing at least one group —$SO_3M$, with M representing a hydrogen atom, an ammonium ion $NH_4^+$ or a metal ion such as, for example, an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such a group —$SO_3M$ may be used in particular.

The aromatic nucleus of the difunctional aromatic monomer also bearing a group —$SO_3M$ as described above may be chosen, for example, from benzene, naphthalene, anthracene, biphenyl, oxybiphenyl, sulfonylbiphenyl and methylenebiphenyl nuclei. As examples of difunctional aromatic monomers also bearing a group —$SO_3M$, mention may be made of: sulfoisophthalic acid, sulfoterephthalic acid, sulfophthalic acid, 4-sulfonaphthalene-2,7-dicarboxylic acid.

The copolymers preferably used are those based on isophthalate/sulfoisophthalate, and more particularly copolymers obtained by condensation of diethylene glycol, cyclohexanedimethanol, isophthalic acid and sulfoisophthalic acid.

The composition according to the invention may also comprise at least one film-forming polymer of natural origin.

Film Forming Polymer of Natural Origin

The film-forming polymers of natural origin, optionally modified, may be chosen from shellac resin, sandarac gum, dammar resins, elemi gums, copal resins and cellulose polymers, and mixtures thereof.

According to one embodiment of the composition according to the invention, the film-forming polymer may be a water-soluble polymer and may be present in an aqueous phase of the first and/or second composition; the polymer is thus solubilized in the aqueous phase of the composition.

According to another embodiment variant of the composition according to the invention, the film-forming polymer may be a polymer dissolved in a liquid fatty phase comprising organic solvents or oils such as those described above (the film-forming polymer is thus said to be a liposoluble polymer). The liquid fatty phase preferably comprises a volatile oil, optionally mixed with a non-volatile oil, the oils possibly being chosen from those mentioned above.

Examples of liposoluble polymers that may be mentioned are copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (containing from 8 to 28 carbon atoms), an alkyl vinyl ether (in which the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate.

Examples of these copolymers that may be mentioned are the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Examples of liposoluble film-forming polymers that may also be mentioned are liposoluble copolymers, and in particular those resulting from the copolymerization of vinyl esters containing from 9 to 22 carbon atoms or of alkyl acrylates or methacrylates, and alkyl radicals containing from 10 to 20 carbon atoms.

Such liposoluble copolymers may be chosen from polyvinyl stearate, polyvinyl stearate crosslinked with the aid of divinylbenzene, of diallyl ether or of diallyl phthalate, polystearyl (meth)acrylate, polyvinyl laurate and polylauryl (meth)acrylate, it being possible for these poly(meth)acrylates to be crosslinked with the aid of ethylene glycol dimethacrylate or tetraethylene glycol dimethacrylate.

The liposoluble copolymers defined above are known and are described in particular in patent application FR-A-2 232 303; they may have a weight-average molecular weight ranging from 2000 to 500 000 and preferably from 4000 to 200 000.

As liposoluble film-forming polymers that may be used in the invention, mention may also be made of polyalkylenes and in particular copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) and in particular copolymers of vinylpyrrolidone and of $C_2$ to $C_{40}$ and better still $C_3$ to $C_{20}$ alkene. As examples of VP copolymers which may be used in the invention, mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

Mention may also be made of silicone resins, which are generally soluble or swellable in silicone oils, which are crosslinked polyorganosiloxane polymers. The nomenclature of silicone resins is known under the name "MDTQ", the resin being described as a function of the various siloxane monomer units it comprises, each of the letters "MDTQ" characterizing a type of unit.

Examples of commercially available polymethylsilsesquioxane resins that may be mentioned include those sold:
by the company Wacker under the reference Resin MK, such as Belsil PMS MK;
by the company Shin-Etsu under the reference KR-220L.

Siloxysilicate resins that may be mentioned include trimethyl siloxysilicate (TMS) resins such as those sold under the reference SR 1000 by the company General Electric or under the reference TMS 803 by the company Wacker. Mention may also be made of the trimethyl siloxysilicate resins sold in a solvent such as cyclomethicone, sold under the name KF-7312J by the company Shin-Etsu, and DC 749 and DC 593 by the company Dow Corning.

Mention may also be made of silicone resin copolymers such as those mentioned above with polydimethylsiloxanes, for instance the pressure-sensitive adhesive copolymers sold by the company Dow Corning under the reference Bio-PSA and described in document U.S. Pat. No. 5,162,410, or the silicone copolymers derived from the reaction of a silicone resin, such as those described above, and of a diorganosiloxane, as described in document WO 2004/073 626.

According to one embodiment of the invention, the film-forming polymer is a film-forming linear block ethylenic polymer, which preferably comprises at least a first block and at least a second block with different glass transition temperatures (Tg), the said first and second blocks being linked together via an intermediate block comprising at least one constituent monomer of the first block and at least one constituent monomer of the second block.

Advantageously, the first and second blocks of the block polymer are mutually incompatible.

Such polymers are described, for example, in document EP 1 411 069 or WO 04/028 488.

The film-forming polymer may also be present in the first and/or second composition in the form of particles dispersed in an aqueous phase or in a non-aqueous solvent phase, which is generally known as a latex or pseudolatex. The techniques for preparing these dispersions are well known to those skilled in the art.

Aqueous dispersions of film-forming polymers that may be used include the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760® by the company Interpolymer, Allianz OPT by the company Rohm & Haas, aqueous dispersions of acrylic or styrene/acrylic polymers sold under the brand name Joncryl® by the company Johnson Polymer, or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulfopolyesters sold under the brand name Eastman AQ® by the company Eastman Chemical Products, and vinyl dispersions, for instance Mexomer PAM® from the company Chimex, and mixtures thereof.

Examples of non-aqueous film-forming polymer dispersions that may also be mentioned include acrylic dispersions in isododecane, for instance Mexomer PAP® from the company Chimex, and dispersions of particles of a grafted ethylenic polymer, preferably an acrylic polymer, in a liquid fatty phase, the ethylenic polymer advantageously being dispersed in the absence of additional stabilizer at the surface of the particles as described especially in document WO 04/055 081, The composition according to the invention may comprise at least one plasticizer that promotes the formation of a film with the film-forming polymer. Such a plasticizer may be chosen from any compound known to those skilled in the art as being capable of fulfilling the desired function.

The composition according to the invention may also comprise at least one dyestuff.

Dyestuff(s)

The composition according to the invention may also comprise at least one dyestuff chosen from pulverulent dyes, liposoluble dyes and water-soluble dyes.

The pulverulent dyestuffs may be chosen from pigments and nacres.

The pigments may be white or coloured, mineral and/or organic, and coated or uncoated. Among the mineral pigments that may be mentioned are titanium dioxide, optionally surface-treated, zirconium oxide, zinc oxide or cerium oxide, and also iron oxide or chromium oxide, manganese violet, ultramarine blue, chromium hydrate and ferric blue. Among the organic pigments that may be mentioned are carbon black, pigments of D&C type, and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with, especially, ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

The dyestuff(s) may be present in the composition according to the invention in a content ranging from 0.01% to 30% by weight relative to the total weight of the said composition.

The composition according to the invention may also comprise at least one filler.

Filler(s)

The fillers may be chosen from those that are well known to those skilled in the art and commonly used in cosmetic compositions. The fillers may be mineral or organic, and lamellar or spherical. Mention may be made of talc, mica, silica, kaolin, polyamide powders, for instance the Nylon® sold under the trade name Orgasol® by the company Arkema France, poly-β-alanine powders and polyethylene powders, powders of tetra-fluoroethylene polymers, for instance Teflon®, lauroyllysine, starch, boron nitride, expanded polymeric hollow microspheres such as those of polyvinylidene chloride/-acrylonitrile, for instance the products sold under the name Expancel® by the company Nobel Industrie, acrylic powders, such as those sold under the name Polytrap® by the company Dow Corning, polymethyl methacrylate particles and silicone resin microbeads, for instance those sold under the name Tospearl® by the company Toshiba, precipitated calcium carbonate, magnesium carbonate and magnesium hydrogen carbonate, hydroxyapatite, hollow silica microspheres such as those sold under the name Silica Beads® by the company Maprecos, glass or ceramic microcapsules, metal soaps derived from organic carboxylic acids containing from 8 to 22 carbon atoms and in particular from 12 to 18 carbon atoms, for example zinc, magnesium or lithium stearate, zinc laurate and magnesium myristate.

It is also possible to use a compound that is capable of swelling on heating, and especially heat-expandable particles such as non-expanded microspheres of copolymer of vinylidene chloride/acrylonitrile/methyl methacrylate or of acrylonitrile homopolymer copolymer, for instance those sold, respectively, under the references Expancel® 820 DU 40 and Expancel® 007WU by the company Akzo Nobel.

The filler(s) may represent from 0.1% to 25% and in particular from 1% to 20% by weight relative to the total weight of the composition.

The dyestuff(s) and/or the filler(s) may also be present in the form of a "particulate paste".

When it contains particles that are solid at room temperature, the composition according to the invention is prepared by introducing them into the composition in the form of a colloidal dispersion also known as a "particulate paste", as described in patent application WO 02/39961, the content of which is incorporated by reference into the present patent application.

For the purposes of the invention, the terms "colloidal dispersion" and "particulate paste" mean a concentrated colloidal dispersion of coated or uncoated particles in a continuous medium, stabilized with a dispersant or optionally without dispersant. These particles may be chosen from pigments, nacres and solid fillers, and mixtures thereof. These particles may be in any form, especially spherical or elongated form such as fibres. They are insoluble in the medium.

The dispersant serves to protect the dispersed particles against agglomeration or flocculation. The dispersant concentration generally used to stabilize a colloidal dispersion is from 0.3 to 5 mg/m$^2$ and preferably from 0.5 to 4 mg/m$^2$ of surface area of particles. This dispersant may be a surfactant, an oligomer, a polymer or a mixture of several thereof, bearing one or more functionalities that have strong affinity for the surface of the particles to be dispersed. In particular, they may physically or chemically attach to the surface of the pigments. These dispersants also have at least one functional group that is compatible with or soluble in the continuous medium. In particular, 12-hydroxystearic acid esters, in particular of a $C_8$ to $C_{20}$ fatty acid and of a polyol such as glycerol or diglycerol, are used, such as poly(12-hydroxystearic acid) stearate with a molecular weight of about 750 g/mol, such as the product sold under the name Solsperse® 21000 by the company Avecia, polyglyceryl-2 dipolyhydroxystearate (CTFA name) sold under the reference Dehymyls® PGPH by the company Henkel, or polyhydroxystearic acid, such as the product sold under the reference Arlacel® P100 by the company Uniqema, and mixtures thereof.

As other dispersants that may be used in the composition of the invention, mention may be made of quaternary ammonium derivatives of polycondensed fatty acids, such as Solsperse® 17000 sold by the company Avecia, and polydimethylsiloxane/oxypropylene mixtures such as those sold by the company Dow Corning under the references DC2-5185 and DC2-5225 C.

The polydihydroxystearic acid and the 12-hydroxystearic acid esters are preferably intended for a hydrocarbon-based or fluoro medium, whereas the oxyethylene/oxypropylene dimethylsiloxane mixtures are preferably intended for a silicone medium.

The colloidal dispersion is a suspension of particles generally of micron size (<10 μm) in a continuous medium. The volume fraction of particles in a concentrated dispersion is from 20% to 40% and preferably greater than 30%, which corresponds to a weight ratio that may be up to 70% according to the density of the particles.

The particles dispersed in the medium may be formed from mineral or organic particles or mixtures thereof such as those described hereinbelow.

The continuous medium of the paste may be any medium and may contain any solvent or liquid fatty substance, and mixtures thereof. Advantageously, the liquid medium of the particulate paste is one of the liquid fatty substances or oils that it is desired to use in the composition, thus forming part of the liquid fatty phase.

Advantageously, the "particulate paste" or colloidal dispersion is a "pigmentary paste" containing a colloidal dispersion of coated or uncoated coloured particles. These coloured particles are pigments, nacres or a mixture of pigments and/or nacres.

Advantageously, the colloidal dispersion represents from 0.5% to 30%, better still from 2% to 20% and even better still from 2% to 15% by weight of the composition.

The composition according to the invention may also comprise at least one fibre.

Fibres

The term "fibre" should be understood as meaning an object of length L and diameter D such that L is very much greater than D, D being the diameter of the circle in which the cross section of the fibre is inscribed. In particular, the ratio L/D (or shape factor) is chosen in the range from 3.5 to 2500, especially from 5 to 500 and in particular from 5 to 150.

The fibres that may be used in the composition of the invention may be mineral or organic fibres of synthetic or natural origin. They may be short or long, individual or organized, for example braided, and hollow or solid. They may have any shape, and may especially have a circular or polygonal (square, hexagonal or octagonal) cross section, depending on the intended specific application. In particular, their ends are blunt and/or polished to prevent injury.

In particular, the fibres have a length ranging from 1 µm to 10 mm, preferably from 0.1 mm to 5 mm and better still from 0.3 mm to 3.5 mm. Their cross section may be within a circle of diameter ranging from 2 nm to 500 µm, preferably ranging from 100 nm to 100 µm and better still from 1 µm to 50 µm. The weight or yarn count of the fibres is often given in denier or decitex, and represents the weight in grams per 9 km of yarn. In particular, the fibres according to the invention may have a yarn count chosen in the range from 0.15 to 30 denier and better still from 0.18 to 18 denier.

The fibres that may be used in the composition of the invention may be chosen from rigid or non-rigid fibres, and may be of synthetic or natural, mineral or organic origin.

Moreover, the fibres may or may not be surface-treated, may be coated or uncoated, and may be coloured or uncoloured.

As fibres that may be used in the composition according to the invention, mention may be made of non-rigid fibres such as polyamide (Nylon®)fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours.

The fibres may be present in the composition according to the invention in a content ranging from 0.01% to 10% by weight, in particular from 0.1% to 5% by weight and more particularly from 0.3% to 3% by weight relative to the total weight of the composition.

The compositions according to the invention may also comprise any additive usually used in cosmetics, such as antioxidants, preserving agents, fragrances, neutralizers, thickeners, vitamins, moisturizers, screening agents, in particular sunscreens, coalescers and plasticizers, and mixtures thereof.

Needless to say, a person skilled in the art will take care to select the optional additional additives and/or the amount thereof such that the advantageous properties of the compositions according to the invention are not, or are not substantially, adversely affected by the envisaged addition.

The compositions according to the present invention, i.e. in particular characterized by its hardness, may be obtained by "cold-tempering" compositions that may themselves be prepared according to various methods known to those skilled in the art.

The "Cold-Tempering" Method

This cold tempering consists in treating the composition obtained according to the standard methods, especially in wax-in-water emulsion form, under cooling conditions such that the composition acquires a hardness in accordance with the invention, for example by placing the composition in a refrigerated chamber.

In particular, the tempering consists in performing cooling for a period of between 15 and 60 minutes at a temperature of between −30° C. and 10° C. and in particular between −28° C. and 0° C., for example by placing in a freezer.

The air may be stirred to obtain a homogeneous temperature in the chamber.

According to one embodiment, the composition is obtained according to the process comprising the following successive steps of:

(i) heating the fatty and aqueous phases in accordance with the invention to a temperature of between 80° C. and 100° C. and more particularly between 85° C. and 100° C., for example to a temperature of 95° C., (ii) emulsifying the said phases especially using a Moritz blender, as is conventionally performed for the production of a mascara in order to obtain a composition according to the invention, (iii) hot-casting of the composition obtained in the preceding step (ii) in a conditioning device, and then (iv) placing the assembly in a freezer, especially at a temperature of between −30° C. and 10° C., for example at a temperature of −28° C., for a period of between 15 and 60 minutes, for example for 45 minutes.

In the context of the present invention, the removal of heat in accordance with the invention may be obtained via any method known to those skilled in the art. Thus, various methods, especially industrial methods, may be used, such as casting the emulsion through a cold tunnel, applying pulsed air, etc.

Advantageously, the composition according to the invention is in the form of a stick, especially a mascara stick.

In addition, the composition according to the invention may be packaged in a conditioning and application device comprising at least:

i. one stick comprising a cosmetic composition as defined previously;

ii. one support for the said stick; and iii. optionally at least one application element, the said application element also possibly being equipped with members for separating and/or combing keratin fibres.

The composition according to the invention may be conditioned as proposed in patent application EP 1 913 835. As illustrated in FIG. 1, the device 1 for conditioning and applying a cosmetic composition P according to the invention in the form of a stick may comprise a plate on which the said stick rests, a pipe 2 forming a housing for the said stick of composition P, the said plate being inside the said pipe, and a means 5 for imposing a translational movement on the plate in the pipe, the said movement of the plate allowing the said composition to be dispensed via a dispensing aperture 9 at the top end of the pipe.

The pipe is stood on a base 3 and that has a bottom 8 and a side wall 7.

The dispensing aperture is bounded by separating/combing members 6, which are advantageously in the form of a row of tapered teeth, of conical structure with a circular base, uniformly distributed along the edge of the dispensing aperture 9. Inside the pipe is the said stick of composition P resting on the said plate actuated by a push-button 4, which, by means of a drive 5, allows the stick of composition P to be moved along an axis X so as to move the said stick beyond the end of the separating/combing members 6.

The separating and/or combing members 6 may especially be in the form of teeth or bristles, arranged in at least one row extending along at least one side of the dispensing aperture 9, and projecting outwards relative to the said face of the support.

The device may have an application surface that is at least partly convex arranged on one face of the support, the application surface being formed by at least part of the side surface of a stick of the composition according to the invention.

This device 1 enables the composition according to the invention to be applied to the eyelashes according to a coating process described hereinbelow.

The process for coating keratin fibres comprises at least the steps consisting in:

placing the said keratin fibres in contact with at least part of the surface of a stick comprising a cosmetic composition as defined previously; and then effecting a relative movement between the surface of the said stick and the said keratin fibres, so as to bring about erosion of the said stick and the formation of a deposit of at least one coat of the said cosmetic composition on the said keratin fibres.

As shown in FIG. 2, the device 1 shown in FIG. 1 is particularly configured for the application of a pasty product to the eyelashes. Such a device is preferentially used by bringing the device 1 into contact with the base of the eyelashes 10, presenting the major axis Y substantially at a tangent to the cornea. The trajectory that the user imposes on the device 1 to obtain the desired coating of the eyelashes follows a loop in a motion whose components are defined in a plane perpendicular to the cornea and parallel to the bridge of the nose.

The motion is made up of three stages, and corresponds to the movements F1, F2 and F3 represented schematically in FIG. 2.

The process can then advantageously be continued by the following steps consisting in:
- retracting the stick inside the device 1, especially inside the pipe 2, below the separating/combing members 6; and then
- separating and/or combing the eyelashes 10 according to the same movements F1, F2 and F3 as for the application of the composition P to the said eyelashes via the said separating/combing members 6.

The examples that follow are given as non-limiting illustrations of the invention. Unless otherwise mentioned, the percentages are expressed on a weight basis relative to the total weight of the composition under consideration.

All the examples and comparative examples 1 to 31 below were performed according to the following protocol:

The fatty and aqueous phases are heated to a temperature of 95° C. and then emulsified using a Moritz blender, as is conventionally performed for the production of a mascara. The emulsion obtained is then hot-cast in a conditioning device, and the assembly is then placed in a freezer at a temperature of –28° C. for 45 minutes so as to obtain after this period solid sticks 8 mm in diameter.

EXAMPLES AND COMPARATIVE EXAMPLES 1 TO 27

TABLE 1

Common formulation for Examples 1 to 20 below, referred to as architecture A

| Trivial name | INCI name | % |
|---|---|---|
| wax | | 20.1 |
| propyl p-hydroxybenzoate | propylparaben | 0.20 |
| oxyethylenated stearyl alcohol | Steareth-2 | 3.33 |
| black iron oxide | CI 77499 | 7.14 |
| mixture of polydimethylsiloxane and hydrated silica | simethicone | 0.13 |
| methyl p-hydroxybenzoate | methyl paraben | 0.15 |
| clean microbiological deionized water | water | 58.78 |
| potassium cetyl phosphate | potassium cetyl phosphate | 5.29 |
| hydroxyethylcellulose | hydroxyethylcellulose | 0.89 |
| gum arabic | acacia | 3.39 |
| 2-phenoxyethanol | phenoxyethanol | 0.60 |

TABLE 2

Common formulation for Examples 21 to 27, referred to hereinbelow as architecture B

| INCI name | (%) |
|---|---|
| Waxes | 20.1 |
| Propylparaben | 0.2 |
| Steareth-2 | 3.33 |
| CI77266 (Black 2) (Distinctive Ink Black LO AQ from Distinctive Cosmetic Ingredients) | 2 |
| Simethicone | 0.13 |
| Methyl paraben | 0.23 |
| Glycerol | 5 |
| Water | 58.94 |
| Potassium cetyl phosphate | 5.29 |
| hydroxyethylcellulose | 0.89 |
| Acacia | 3.39 |
| Phenoxyethanol | 0.60 |

The nature of the waxes of the various Examples and Comparative Examples 1 to 27 are given in Table 3 below. Table 3 also mentions the content of wax(es), the solids content (SC) in the composition, the structure obtained, and also the shear hardness of a stick in accordance with the definition according to the invention for each of the Examples and Comparative Examples 1 to 27.

The theoretical solids content of these examples and comparative examples is 41.22% by weight relative to the total weight of the composition.

NA in Table 3 means that the measurement is not significant.

TABLE 3

| Tests | Ex. 1 (invention) Architecture A | Ex. 2 (comparative) Architecture A | Ex. 3 (invention) Architecture A | Ex. 4 (comparative) Architecture A | Ex. 5 (comparative) Architecture A | Ex. 6 (invention) Architecture A |
|---|---|---|---|---|---|---|
| Waxes included in the formulation | 3.2% carnauba wax 4% natural beeswax 12.9% paraffin | 20.1% natural beeswax | 20.1% carnauba wax | 20.1% rice bran wax | 20.1% phytowax olive | 20.1% synthetic beeswax (Cyclochem 326 A from Evonik Goldschmidt) |
| Dry extract (weight %) | 39.1 | 42.6 | 44.2 | 42.4 | 43.0 | 36.6 |
| Structure | stick | no stick | Stick* | no stick | no stick | stick |
| Shear hardness of the stick (in g) | 5.0 ± 0.1 | NA | 10.7 ± 0.8 | NA | NA | 5.3 ± 0.5 |

TABLE 3-continued

| Tests | | | | | | |
|---|---|---|---|---|---|---|
| Shear hardness of the stick (in g/m) | 625 ± 12.5 | NA | 1337.5 ± 100 | NA | NA | 662.5 ± 62.5 |

| Tests | Ex. 7 (comparative) Architecture A | Ex. 8 (comparative) Architecture A | Ex. 9 (comparative) Architecture A | Ex. 10 (comparative) Architecture A | Ex. 11 (comparative) Architecture A | Ex. 12 (invention) Architecture A |
|---|---|---|---|---|---|---|
| Waxes included in the formulation | 20.1% candelilla wax | 20.1% hydrogenated jojoba oil | 20.1% polyethylene wax (Performalene 500-L Polyethylene from New Phase Technologies) | 20.1% ozokerite | 20.1% paraffin | 5% carnauba wax + 15.1% hydrogenated olive oil esterified with stearyl alcohol (Phytowax Olive 18L57 sold by the company Sophim) |
| Dry extract (weight %) | 41.2 | 38.3 | 42.6 | 41.0 | 41.7 | 39.6 |
| Structure | no stick | no stick | no stick | No stick | No stick | stick |
| Shear hardness of the stick (in g) | NA | NA | NA | NA | NA | 5.0 ± 0.4 |
| Shear hardness of the stick (in g/m) | NA | NA | NA | NA | NA | 625 ± 50 |

| Tests | Ex. 13 (invention) Architecture A | Ex. 14 (invention) Architecture A | Ex. 15 (invention) Architecture A | Ex. 16 (invention) Architecture A | Ex. 17 (invention) Architecture A |
|---|---|---|---|---|---|
| Waxes included in the formulation | 5% Carnauba + 15.1% beeswax | 5% Carnauba + 15.1% paraffin | 5% Carnauba + 15.1% Polyethylene | 5% Carnauba + 15.1% ozokerite | 5% synthetic beeswax 15.1% ozokerite |
| Dry extract (weight %) | 39.4 | 38.5 | 38.9 | 39.3 | 38.0 |
| Structure | stick | stick | stick | stick | stick |
| Shear hardness of the stick (in g) | 4.0 ± 0.1 | 7.0 ± 1.0 | 10.0 ± 1.0 | 9.0 ± 1.9 | 3.0 ± 0.1 |
| Shear hardness of the stick (in g/m) | 500 ± 12.5 | 875 ± 12.5 | 1250 ± 12.5 | 1125 ± 237.5 | 375 ± 12.5 |

| Tests | Ex. 18 (invention) Architecture A | Ex. 19 (invention) Architecture A | Ex. 20 (invention) Architecture A | Ex. 21 (comparative) Architecture B |
|---|---|---|---|---|
| Waxes included in the formulation | 1% synthetic beeswax + 4% Carnauba + 15.1% ozokerite | 4% synthetic beeswax + 1% Carnauba + 15.1% ozokerite | 2.5% synthetic beeswax + 2.5% Carnauba + 15.1% ozokerite | 20.1% microcrystalline wax (Base Wax 30540 or Microwax HW from Paramelt) |
| Dry extract (weight %) | 38.4 | 35.6 | 35.9 | 31.4 |
| Structure | stick | stick | stick | no stick |
| Shear hardness of the stick (in g) | 8.2 ± 0.8 | 3.7 ± 0.8 | 4.4 ± 0.9 | NA |
| Shear hardness of the stick (in g/m) | 1025 ± 100 | 462.5 ± 100 | 550 ± 112 | NA |

TABLE 3-continued

| Tests | Ex. 22 (comparative) Architecture B | Ex. 23 (comparative) Architecture B | Ex. 24 (comparative) Architecture B | Ex. 25 (comparative) Architecture B | Ex. 26 (comparative) Architecture B | Ex. 27 (invention) Architecture B |
|---|---|---|---|---|---|---|
| Waxes included in the formulation | 20.1% polyethylene wax (Performalene 400 Polyethylene from New Phase Technologies) | 20.1% $C_{20\text{-}40}$ alkyl stearate (Kester Wax K82H from Koster Keunen) | 20.1% $C_{20}$-$C_{40}$ alkyl (hydroxystearyloxy)stearate (Kester Wax K82P from Koster Keunen) | 20.1% Polyglycerolated beeswax (Cera Bellina Wax from Koster Keunen) | 1% Carnauba + 19.1% ozokerite | 4% Carnauba + 1% synthetic beeswax + 15.1% ozokerite |
| Dry extract (weight %) | Not measured | 40.5 | 30.9 | 30.1 | 31.9 | 33.6 |
| Structure | No stick | No stick | No stick | No stick | No stick | stick |
| Shear hardness of the stick (in g) | NA | NA | NA | NA | NA | 6.2 ± 0.8 |
| Shear hardness (in g/m) | NA | NA | s | NA | NA | 775 ± 100 |

*stick appearance: smooth and hard

EXAMPLE 28

The composition of Example 28 according to the invention is presented in Table 4 below. The shear hardness is expressed in grams (and converted into g/m).

TABLE 4

| Ex. 28 (invention) | |
|---|---|
| INCI name | (%) |
| Carnauba wax | 2.5 |
| Ozokerite | 14.1 |
| Propyl paraben | 0.2 |
| Steareth-2 | 2.77 |
| CI77266 (Black 2) (Distinctive Ink Black LO AQ from Distinctive Cosmetic Ingredients) | 1.66 |
| Simethicone | 0.11 |
| Methyl paraben | 0.15 |
| Glycerol | 4.16 |
| Water | 65.82 |
| Potassium cetyl phosphate | 4.4 |
| Hydroxyethylcellulose | 0.72 |
| Acacia | 2.81 |
| Phenoxyethanol | 0.60 |
| Solids content (%) | 25.9 |
| Shear hardness (in g) | 2 g ± 0.1 |
| Shear hardness (in g/m) | 250 ± 12.5 |

It emerges from these tests of Examples 1 to 28 that the presence of carnauba wax and/or synthetic beeswax in a content of at least 2% by weight relative to the total weight of the composition is essential for producing a composition of hardness in accordance with the invention and in particular for producing a stick. A choice was thus made among the cosmetic waxes commonly used for the preparation of mascara compositions.

EXAMPLE 29

The composition of Example 29 according to the invention is presented in Table 3 below. The shear hardness is expressed in grams (and converted into g/m).

TABLE 5

| Ex. 29 (invention) | |
|---|---|
| INCI name | (%) |
| Carnauba wax | 4 |
| Synthetic beeswax | 1 |
| Ozokerite | 15 |
| Propyl paraben | 0.2 |
| Steareth-2 | 5.29 |
| CI77266 (Black 2) (Distinctive Ink Black LO AQ from Distinctive Cosmetic Ingredients) | 2 |
| Simethicone | 0.13 |
| Methyl paraben | 0.23 |
| Glycerol | 5 |
| Water | 58.94 |
| Potassium cetyl phosphate | 3.33 |
| Hydroxyethylcellulose | 0.89 |
| Acacia | 3.39 |
| Phenoxyethanol | 0.60 |
| Solids content (%) | 33.7 |
| Shear hardness (in g) | 7.5 g ± 0.9 |
| Shear hardness (in g/m) | 937.5 ± 112.5 |

A stick of the required shear hardness is obtained, which allows a uniform deposit to be applied to the eyelashes, especially using a device according to the attached figures.

EXAMPLES 30-31

The compositions of the Examples and Comparative Examples 30 and 31 are presented in Table 6 below. The shear hardness is expressed in grams and in g/m.

TABLE 6

| Tests | | Ex 30 (comparative) (%) | Ex 31 (invention) (%) |
|---|---|---|---|
| Trivial name | INCI name | | |
| Glyceryl stearate (Tegin M Pellets from Evonik Goldschmidt) | Glyceryl stearate | 2.15 | 2.15 |

TABLE 6-continued

| Tests | | Ex 30 (comparative) | Ex 31 (invention) |
|---|---|---|---|
| Trivial name | INCI name | (%) | (%) |
| Glyceryl stearate PEG-30 (Tagat S from Evonik Goldschmidt) | PEG-30 glyceryl stearate | 5.54 | 5.54 |
| Blanched beeswax | Cera alba | 7.16 | 9.32 |
| Hydrogenated jojoba oil | Hydrogenated jojoba oil | 7.16 | 0 |
| Carnauba wax | Cera Carnauba | 0 | 5 |
| Butyl p-hydroxybenzoate | Butyl paraben | 0.12 | 0.12 |
| Ethyl p-hydroxybenzoate | Ethyl paraben | 0.10 | 0.10 |
| Polybutene (95/5 monoolefins/isoparaffins) (MW = 2060) | polybutene | 1.00 | 1.00 |
| Technical-grade N-oleyldihydroshingosine | 2-oleamido-1,3-octadecanediol | 0.10 | 0.10 |
| Black iron oxide | CI 77499 | 7.00 | 7.00 |
| Polyquaternium-4 | Polyquaternium-4 | 3.87 | 3.87 |
| Deionized water | aqua | 65.31 | 65.31 |
| Glycerol | Glycerol | 0.10 | 0.10 |
| Methyl p-hydroxybenzoate | Methyl paraben | 0.24 | 0.24 |
| EDTA | Disodium EDTA | 0.10 | 0.10 |
| Pure sodium hydroxide | Sodium hydroxide | 0.05 | 0.05 |

Table 7 below collates the state of aggregation, the structure and the shear hardness of a stick having the composition of Example 32 or 33.

TABLE 7

| | Ex 32 | Ex 33 |
|---|---|---|
| State of aggregation | No aggregate | Aggregate |
| Solids content (%) | 35.3 | 35.8 |
| Structure | No stick | stick |
| Shear hardness of the stick (in g) | NA | 6.4 ± 0.5 |
| Shear hardness of the stick (in g/m) | NA | 800 ± 62,.5 |

The stick as obtained in Example 33 allows a uniform deposit to be applied to the eyelashes, especially using a device according to the attached figures.

EXAMPLES 32

Hardness of Sticks

This example consisted in studying, on the one hand, the impact of the cooling kinetics on the structuring of a stick, and, on the other hand, the hardness of a stick as a function of the cooling time.

For this example, the cooling used is that of placing the composition in a refrigerated chamber at −28° C.

For these two studies, a stick was prepared according to the following composition:

| | | INCI name | Trivial name |
|---|---|---|---|
| Phase A | 4.00% | Cera carnauba | Carnauba wax |
| | 15.00% | Ozokerite | Ozokerite |
| | 1.00% | Synthetic beeswax | Synthetic beeswax |
| | 0.20% | Propyl paraben | Propyl paraben |
| | 3.33% | Steareth-2 | Oxyethylenated stearyl alcohol |
| Phase B1 | 0.15% | Methyl paraben | Methyl paraben |
| | 22.72% | Aqua | Water |
| | 0.13% | Simethicone | Simethicone |
| | 5.29% | Potassium cetyl phosphate | Potassium cetyl phosphate |
| Phase B2 | 5.00% | Glycerol | Glycerol |
| | 10.00% | CI 77266 (20%) dispersion in acacia and aqua | Carbon black as a dispersion in a gum arabic gel |
| | 0.9% | Hydroxyethylcellulose | Hydroxyethylcellulose |
| | 2.84% | Acacia | Gum Arabic |
| | 0.6% | Phenoxyethanol | Phenoxyethanol |
| | qs 100 | Aqua | Water |

The protocol for preparing the stick from the emulsion was varied in order to successfully complete the study, the objectives of which have been mentioned above.

According to a first section of the study, the cooling kinetics were modulated.

Thus, the first consisted in leaving the product to cool to room temperature.

The second consisted in cooling the product by placing it in a refrigerated chamber at −28° C. for 45 minutes.

Figure 3:
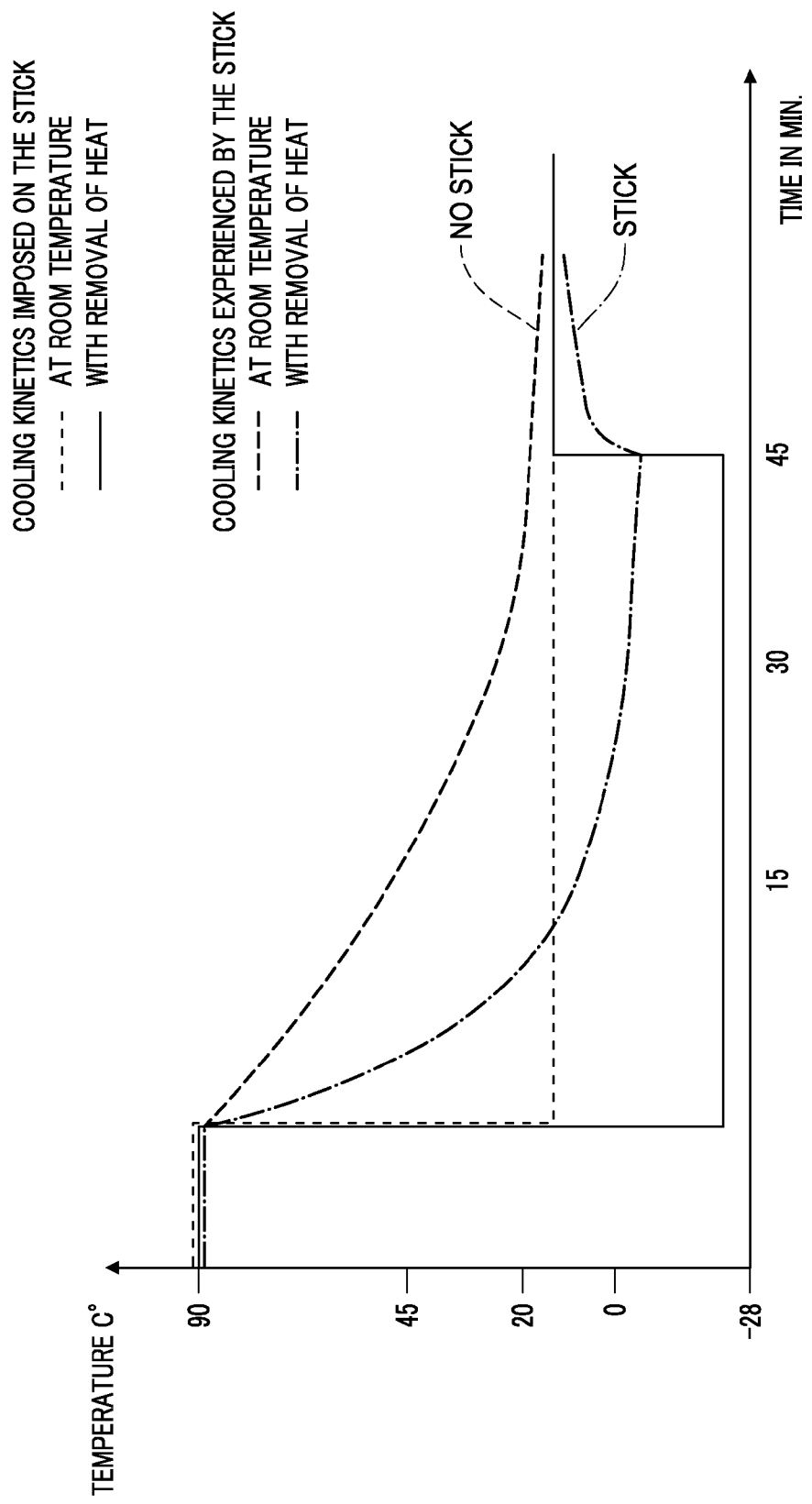

As reported in the attached FIG. 3, it is observed that a stick is or is not obtained, depending on the kinetics adopted. This study illustrates the fact that in order to obtain the required structuring, enabling hardnesses suitable for the use intended in the context of the present invention to be obtained, a removal of heat allowing a lowering of the temperature of the composition to less than 4° C., or even less than 1° C., in less than 30 minutes should advantageously be applied.

Figure 4:
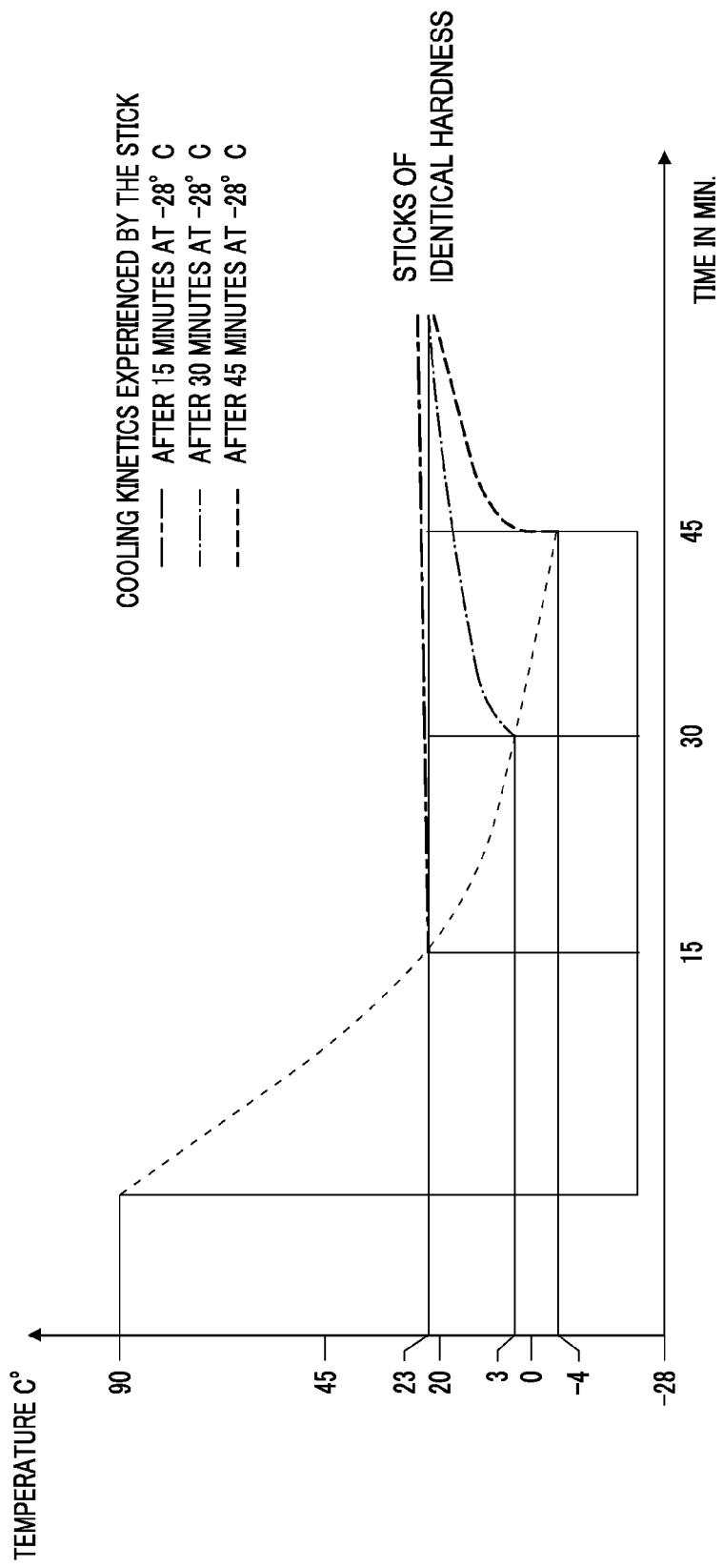

As illustrated in the attached FIG. 4, it is observed that provided that the removal of heat recalled above is applied, sticks of identical hardness are obtained irrespective of the cooling time used.

The invention claimed is:

1. A cosmetic composition in stick form, which can be applied dry, for caring for and/or making up keratin fibers, (i) which is in the form of an emulsion comprising a fatty phase dispersed in an aqueous phase, the said fatty phase comprising carnauba wax and/or synthetic beeswax, in a content of at least 2% by weight relative to the total weight of the said composition, and (ii) which has a shear hardness of between 375 g/m and 5000 g/m, the said shear hardness being measured at 20° C. on a cylindrical stick, using a rigid tungsten wire 250 μm in diameter, by advancing the wire relative to the stick at a rate of 100 mm/minute, the composition comprising less than 5% of a liquid fatty phase, the composition also comprising at least one emulsifier selected from the group consisting of anionic surfactants selected from the group consisting of salts of $C_{16}$-$C_{30}$ fatty acids, salts of polyoxyethylenated fatty acids, phosphoric esters and salts thereof, sulfosuccinates, alkyl ether sulfates, isethionates, acylglutamates, soybean derivatives, citrates, proline derivatives, lactylates, sarcosinates, sulfonates and glycinates, non-ionic surfactants with an HLB of greater than or equal to 8 at 25° C., and mixtures thereof, the composition being obtained via a process comprising at least one step that involves a removal of heat that lowers the temperature of the composition to less than 4° C. in less than 30 minutes.

2. The composition according to claim 1, wherein the carnauba wax and/or the synthetic beeswax is included in a content of at least 3% by weight, relative to the total weight of the said composition.

3. The composition according to claim 1, wherein the shear hardness is between 500 g/m and 2500 g/m.

4. The composition according to claim 1, wherein it has a solids content of less than or equal to 45% by weight, relative to the total weight of the said composition.

5. The composition according to claim 1, wherein it also comprises at least one additional wax, other than synthetic beeswax and carnauba wax, selected from the group consisting of waxes that are solid at room temperature, optionally in the form of an aqueous wax dispersion, of animal, plant, mineral or synthetic origin, and mixtures thereof, and/or having a tack of greater than or equal to 0.7 N.s and a hardness of less than or equal to 3.5 MPa.

6. The composition according to claim 5, wherein the additional wax is selected from the group consisting of (i) hydrocarbon-based waxes selected from the group consisting of natural beeswax (or blanched beeswax), lanolin wax, Chinese insect waxes, rice wax, candelilla wax, ouricury wax, esparto grass wax, cork fiber wax, sugarcane wax, Japan wax, sumach wax, montan wax, microcrystalline waxes, paraffins, ozokerite, polyethylene waxes, the waxes obtained by Fischer-Tropsch synthesis, waxy copolymers and esters thereof, (ii) the waxes obtained by catalytic hydrogenation of animal or plant oils containing linear or branched $C_8$-$C_{32}$ fatty chains, (iii) silicone waxes, (iv) fluoro waxes, (v) the wax obtained by hydrogenation of olive oil esterified with stearyl alcohol, and (vi) the waxes obtained by hydrogenation of castor oil esterified with cetyl alcohol.

7. The composition according to claim 1, wherein it also comprises ozokerite wax.

8. The composition according to claim 1, wherein it has a total content of wax(es) of between 2% and 35% by weight.

9. The composition according to claim 1, wherein it comprises at least one anionic surfactant selected from the group consisting of salts of $C_{16}$-$C_{30}$ fatty acids, phosphoric esters and salts thereof, and optionally at least one nonionic surfactant selected from the group consisting of oxyethylenated and/or oxypropylenated ethers (which may comprise from 1 to 150 oxyethylene and/or oxypropylene groups) of fatty alcohols; esters of fatty acids (especially of $C_8$-$C_{24}$ and preferably $C_{16}$-$C_{22}$ acids) and of polyols, esters of fatty acids and of oxyethylenated and/or oxypropylenated glycerol ethers (which may comprise from 1 to 150 oxyethylene and/or oxypropylene groups), and mixtures thereof.

10. The composition according to claim 1, wherein it comprises from 0.01% to 30% by weight of emulsifier relative to the total weight of the said composition.

11. A process for coating keratin fibers, comprising at least the steps consisting in:

placing the said keratin fibers in contact with at least part of the surface of a stick comprising a cosmetic composition as defined according to claim 1; and then effecting a relative movement between the surface of the said stick and the said keratin fibers, so as to bring about erosion of the said stick and the formation of a deposit of at least one coat of the said cosmetic composition on the said keratin fibers.

12. A device for conditioning and applying a cosmetic composition for caring for and/or making up keratin fibers, wherein it comprises at least:

one stick comprising a cosmetic composition as defined according to claim 1;

one support for the said stick; and optionally at least one application element, the said application element possibly being equipped with members for separating and/or combing the said keratin fibers.

13. A stick, which can be applied dry, for making up and/or caring for keratin fibers, which may be obtained, or is obtained, via the process comprising at least one of the following steps consisting successively in:

heating a composition containing a fatty phase and an aqueous phase, the said fatty phase comprising carnauba wax and/or synthetic beeswax, in a content of at least 2% by weight relative to the total weight of the said composition, to a temperature of between 80° C. and 100° C., emulsifying the said phases especially using a stirrer so as to obtain a composition of emulsion type with an aqueous continuous phase, hot-casting the said composition in a conditioning device, and then cooling the said composition to temperature of between −30° C. and 10° C., until the composition is in the form of a stick; wherein said composition has a shear hardness of between 375 g/m and 5000 g/m, the said shear hardness being measured at 20° C. on a cylindrical stick, using a rigid tungsten wire 250 μm in diameter, by advancing the wire relative to the stick at a rate of 100 mm/minute.

14. A stick, which can be applied dry, for making up and/or caring for keratin fibers,
- (i) which is in the form of an emulsion comprising a fatty phase dispersed in an aqueous phase, the said fatty phase comprising carnauba wax and/or synthetic beeswax, in a content of at least 2% by weight, relative to the total weight of the said composition,
- (ii) which has a shear hardness of between 375 g/m and 5000 g/m, the said shear hardness being measured at 20° C. on a stick using a rigid tungsten wire 250 μm in diameter, by advancing the wire relative to the stick at a rate of 100 mm/minute,
- (iii) the said stick being obtained via a process comprising at least the following steps consisting successively in:

heating the said emulsion to a temperature of between 80° C. and 100° C., emulsifying the said phases especially using a stirrer so as to obtain a composition of emulsion type with an aqueous continuous phase, hot-casting the said composition in a conditioning device, and then removing heat, to allow a lowering of the stick temperature to less than 4° C. in less than 30 minutes.

15. The composition according to claim 1, wherein the composition further comprises at least one non-ionic surfactant with an HLB of less than 8 at 25° C.

* * * * *